United States Patent
Watanabe et al.

(10) Patent No.: US 11,008,365 B2
(45) Date of Patent: May 18, 2021

(54) POLYPEPTIDE EXHIBITING AFFINITY TO ANTIBODIES FORMING NON-NATIVE THREE-DIMENSIONAL STRUCTURE

(71

(56) References Cited

FOREIGN PATENT DOCUMENTS

WO    2014/115229 A1    7/2014

OTHER PUBLICATIONS

Ricardo L. A. Dias et al., "Protein Ligand Design: From Phage Display to Synthetic Protein Epitope Mimetics in Human Antibody Fc-Binding Peptidomimetics", J. Am. Chem. Soc., vo. 128, 2006, pp. 2726-2732, 7 pages total.
Giorgio Fassina et al., "Protein A Mimetic Peptide Ligand for Affinity Purification of Antibodies", Journal of Molecular Recognition, vol. 9, pp. 564-569 (1996), 6 pages total.
Giorgio Fassina et al., "Immunoglobulin specificity of TG19318: a novel synthetic ligand for antibody affinity purification", Journal of Molecular Recognition, vol. 11, pp. 128-133 (1998), 6 pages total.
George K. Ehrlich et al., "Identification of peptides that bind to the constant region of a humanized $IgG_1$ monoclonal antibody using phage display", Journal of Molecular Recognition, vol. 11, pp. 121-125 (1998), 5 pages total.
Margareta Krook, "Novel peptides binding to the Fc-portion of immunoglobulins obtained from a combinatorial phage display peptide library", Journal of Immunological Methods, vol. 221 (1998) pp. 151-157, 7 pages total.
Antonio Verdoliva et al., "A New Ligand for Immunoglobulin G Subdomains by Screening of a Synthetic Peptide Library", ChemBioChem, vol. 6, pp. 1242-1253, 2005, 12 pages total.
Kotaro Sakamoto et al., "Discovery and Characterization of a Peptide Motif That Specifically Recognizes a Non-native Conformation of Human IgG Induced by Acidic pH Conditions", The Journal of Biological Chemistry vol. 284, No. 15, pp. 9986-9993, Apr. 10, 2009, 9 pages total.
Steven A. Berkowitz et al., "Analytical tools for characterizing biopharmaceuticals and the implications for biosimilars", Nat Rev Drug Discov., vol. 11, No. 7, pp. 527-540, 2012, 26 pages total.
Amy S. Rosenberg, "Effects of Protein Aggregates: An Immunologic Perspective", The AAPS Journal, vol. 8, No. 3, Article 59, pp. E501-E507, 2006, 7 pages total.
Makoto Iguchi et al., "Development and market of antibody Drugs", pp. 59-66, Jul. 2, 2012, 29 pages total.
Sophia Hober, "Protein A chromatography for antibody purification", Journal of Chromatography B, vol. 848 (2007) pp. 40-47, 8 pages total.
Sohei Kanno et al., "Assembling of engineered IgG-binding protein on gold surface for highly oriented antibody immobilization", Journal of Biotechnology, vol. 76 (2000), pp. 207-214, 8 pages total.
Johannes Buchner et al., "Alternatively Folded States of an Immunoglobulin", Biochemistry, vol. 30, pp. 6922-6929, 1991, 8 pages total.
Michael J. W. Thies et al., "The Alternatively Folded State of the Antibody $C_H3$ Domain", J. Mol. Biol. vol. 309, pp. 1077-1085 (2001), 9 pages total.
Matthias Johannes Feige et al., "Dissecting the Alternatively Folded State of the Antibody Fab Fragment", J. Mol. Biol., vol. 399, pp. 719-730, (2010), 12 pages total.
R.H. Pain, "Folding of Proteins", Edition 2, pp. 31-33, 2002, 10 pages total.
Daniel Kanmert et al., "Thermal Induction of an Alternatively Folded State in Human IgG-Fc", Biochemistry, vol. 50, pp. 981-988, 2011, 8 pages total.
Quanzhou Luo et al., "Chemical Modifications in Therapeutic Protein Aggregates Generated under Different Stress Conditions", The Journal of Biological Chemistry, vol. 286, No. 28, pp. 25134-25144, Jul. 15, 2011, 12 pages total.
Marisa K. Joubert et al., "Highly Aggregated Antibody Therapeutics Can Enhance the in Vitro Innate and Late-stage T-cell Immune Responses", The Journal of Biological Chemistry vol. 287, No. 30, pp. 25266-25279, Jul. 20, 2012, 15 pages total.

Shinji Yoshitake et al., "Conjugation of Glucose Oxidase from Aspergillus niger and Rabbit Antibodies Using N-Hydroxysuccinimide Ester of N-(4-Carboxycyclohexylmethyl)-Maleimide", Eur. J. Biochem. vol. 101, pp. 395-399 (1979), 5 pages total.
Yasuro Oshima et al., "Post sequence protein Experimental Method 3, The basis of structure/function analysis", pp. 49-52, 96-98, 115-116, and 128-131, Oct. 15, 2002, 41 pages total.
Adam Brymora et al., "Protein-Protein Interactions Identified by Pull-Down Experiments and Mass Spectrometry", Current Protocols in Cell Biology, Supplement 22, pp. 17.5.1-17.5.51 (2004), 51 pages total.
Ilka Wittig et al., "Native electrophoretic techniques to identify protein-protein interactions", Proteomics, vol. 9, pp. 5214-5223, 2009, 10 pages total.
Sang-Hyun Park et al., "Fluorescence Polarization Assay to Quantify Protein-Protein Interactions", Methods in Molecular Biology, vol. 261: Protein-Protein Interactions: Methods and Protocols, pp. 161-165, 2004, 7 pages total.
Andrew C. Braisted et al., "Minimizing a binding domain from protein A", Proc. Natl. Acad. Sci. USA, vol. 93, pp. 5688-5692, Jun. 1996, 5 pages total.
Hideki Watanabe et al., "Optimizing pH Response of Affinity between Protein G and IgG Fc, How Electrostatic Modulations Affect Protein-Protein Interactions", The Journal of Biological Chemistry vol. 284, No. 18, pp. 12373-12383, May 1, 2009, 12 pages total.
"Bio-Pharmaceutical Handbook—From manufacturing of Biologics to quality management-", Bio-virus Committee, PDA Japan chapter, pp. 41-43, Jan. 25, 2014, 11 pages total.
Hideki Watanabe et al., "Small artificial protein design using minute protein as components", Institute of Advanced Industrial Science and Technology biomedical research division, The 13th Japan Protein Science Society Annual Meeting Program/Collection of Summaries, May 31, 2013, p. 80, total 5 pages.
Hideki Watanabe et al., "Tracing Primordial Protein Evolution through Structurally Guided Stepwise Segment Elongation", The Journal of Biological Chemistry vol. 289, No. 6, pp. 3394-3404, Feb. 7, 2014, 12 pages total.
Aaron L. Nelson, "Antibody fragments, Hope and hype", mAbs, vo. 2, No. 1, pp. 77-83, Jan. 1, 2010, 8 pages total.
Hideki Watanabe et al., "Adaptive Assembly: Maximizing the Potential of a Given Functional Peptide with a Tailor-Made Protein Scaffold", Chemistry & Biology, vol. 22, No. 9, pp. 1165-1173, Sep. 17, 2015, 17 pages total.
Alain Beck et al., "Characterization of Therapeutic Antibodies and Related Products", Anal. Chem. vol. 85, No. 2, pp. 715-736, 22 pages total.
Beatrice M. P. Huyghues-Despointes et al., "Measuring the Conformational Stability of a Protein by Hydrogen Exchange", Methods in Molecular Biology, vol. 168, pp. 69-92, 2001, 24 pages total.
Emmanuel Baslè et al., "Protein Chemical Modification on Endogenous Amino Acids", Chemistry & Biology, vol. 17, pp. 213-227, Mar. 26, 2010, 15 pages total.
M. Amblard et al., "Fundamentals of Modern Peptide Synthesis", *Methods in Molecular Biology*, vol. 298, pp. 3-24, 2005, 22 pages total.
J. H. Lee et al., "High-Level Expression of Antimicrobial Peptide Mediated by a Fusion Partner Reinforcing Formation of Inclusion Bodies", Biochemical and Biophysical Research Communications, vol. 277, No. 3, pp. 575-580 (2000), 6 pages total.
S. N. Davidoff et al., "Surface Plasmon Resonance for Therapeutic Antibody Characterization", Label-Free Biosensor Methods in Drug Discovery, Methods in Pharmacology and Toxicology, pp. 35-76, 2015, 40 pages total.
Mary C. Puckett, "Hexahistidine (6xHis) Fusion-Based Assays for Protein-Protein Interactions", Methods in Molecular Biology, vo. 1278, pp. 365-370, 2015, total 6 pages.
Ronald T. Raines, "Fluorescence Polarization Assay to Quantify Protein-Protein Interactions: An Update", Methods in Molecular Biology, vol. 1278, pp. 323-327, 2015, 5 pages total.
Seiki Yageta et al., "Conformational and Colloidal Stabilities of Isolated Constant Domains of Human Immunoglobulin G and Their

(56) References Cited

OTHER PUBLICATIONS

Impact on Antibody Aggregation under Acidic Conditions", Mol. Pharmaceutics, vol. 12, No. 5, pp. 1443-1455, 2015, 13 pages total.
Farid Khan et al., "Double-Hexahistidine Tag with High-Affinity Binding for Protein Immobilization, Purification, and Detection on Ni-Nitrilotriacetic Acid Surfaces", Anal. Chem., vol. 78, No. 9, pp. 3072-3079, May 1, 2006, 8 pages total.
Joshua Silverman, "Multivalent avimer proteins evolved by exon shuffling of a family of human receptor domains", Nature Biotechnology, vol. 23, No. 12, pp. 1556-1561, Dec. 2005, 6 pages total.
International Search Report dated Apr. 1, 2014 issued by the International Searching Authority in PCT/JP2013/007583.
International Search Report dated Nov. 21, 2017 issued by the International Searching Authority in PCT/JP2013/031315.
Extended European Search Report dated Jun. 6, 2016 issued by the European Patent Office in No. 13873013.0.
Communication dated Feb. 15, 2018 issued by the European Patent Office in No. 13873013.0.
Communication dated Feb. 29, 2016 issued by the United States Patent and Trademark Office in U.S. Appl. No. 14/763,589.
Communication dated Jun. 16, 2016 issued by the United States Patent and Trademark Office in U.S. Appl. No. 14/763,589.
Communication dated Mar. 28, 2018 issued by the European Patent Office in No. 13873013.0.
Communication dated Dec. 6, 2018 issued by the European Patent Office in No. 13873013.0.
Mark R. Bell et al., "To fuse or not to fuse: What is your purpose?", Protein Science, vol. 22, pp. 1466-1477, 2013, 12 pages total.
Hans-Hermann Gerdes et al., "Green fluorescent protein" applications in cell biology, FEBS Letters, vol. 389, pp. 44-47 (1996), 4 pages total.
Mathias Uhlèn et al., "Fusion proteins in biotechnology", Current Opinion in Biotechnology, vol. 3, pp. 363-369, 1992, 7 pages total.
Joakim Nilsson et al., "Competitive elution of protein A fusion proteins allows specific recovery under mild conditions", Eur. J. Bio chem. vol. 224, pp. 103-108 (1994), 6 pages total.

\* cited by examiner

POLYPEPTIDE EXHIBITING AFFINITY TO ANTIBODIES FORMING NON-NATIVE THREE-DIMENSIONAL STRUCTURE

CROSS REFERENCE TO RELATED APPLICATIONS

Related Application

This application is a National Stage of International Application No. PCT/JP2017/031315, filed Aug. 31, 2017, claiming the priority of Japanese Patent Application No. 2016-170867 (filed Sep. 1, 2016), the disclosure of each of which is incorporated herein by reference.

TECHNICAL FIELD

The present invention relates to a polypeptide having a specific affinity for a protein partially including a CH1-CL domain forming a non-native three-dimensional structure among proteins including a CH1-CL domain of an antibody such as immunoglobulin G (IgG) or a Fab region thereof, and to a method for detecting, immobilizing, or removing the protein using the affinity polypeptide.

BACKGROUND ART

The so-called antibody drugs, which utilize monoclonal antibodies for therapeutic applications, have annual sales of more than 30 billion dollars and are the largest biopharmaceutical products and the fastest growing segment in the entire pharmaceutical industry. Until now, 23 full-size monoclonal antibodies have been launched, and some of which are already blockbusters with annual sales of more than one billion dollars. The drug candidate monoclonal antibodies whose clinical trials were initiated from 1995 to 2007 have more than tripled, and the number has continued to grow further (Non Patent Literature 1).

With the progress of clinical application of antibodies, as next generation antibodies, low-molecular-weight antibodies, such as Fab regions, are also being developed as a form of antibody molecules having higher tissue penetration or of antibody molecules with a reduced manufacturing cost (Non Patent Literature 2). As of 2015, three products of Fab regions have been approved as therapeutic antibodies by the FDA. It is expected that such low-molecular-weight antibodies will continue to be developed to complement disadvantages of high-molecular-weight IgG antibodies.

With such growth and expansion of the antibody drugs market, research and development relating to the creation and improvement of molecules having affinity for antibodies have been actively conducted. This is because such molecules are useful for research, manufacture, and analysis of antibodies and so on, particularly because a great demand is expected in affinity purification and quality control at the time of manufacturing antibody drugs.

Currently, research and development of various approaches on polypeptides having affinity for antibodies are being conducted, and some of which will be described below.

Suzuki et al. used a phage library displaying linear peptides of 7 or 12 residues on filamentous bacteriophage M13 for identifying a plurality of polypeptides having affinity for the Fc region of human IgG and measured whether affinity for the Fc region is present or not by enzyme-linked immunosorbent assay (ELISA) (Patent Literature 1). They produced a peptide as the common sequence extracted from the identified plurality of polypeptides and validated the binding of the peptide to human IgG and also validated the affinity for the Fc region of IgG derived from a horse, a rabbit, a guinea pig, a goat, a cat, a dog, a bovine, a pig, and a mouse by ELISA.

DeLano et al. used a phage library displaying cyclic peptides represented by Xaai Cys Xaaj Cys Xaak (wherein i, j, and k are integers satisfying i+j+k=18) circularized through disulfide bonds on filamentous bacteriophage M13 to obtain a plurality of cyclic peptides of 20 residues which competitively react with protein A derived from *Staphylococcus aureus* for binding to human IgG. They further produced a cyclic peptide Fc-III which consisted of 13 residues as the common sequence extracted from these peptides and found that the peptide had a competitive inhibition ability of Ki=100 nM in a competitive reaction with protein A (Non Patent Literature 3) and disclosed that in an experiment using rabbits, the Fab half-life in vivo could be improved by fusing the Fab fragment, which is the antigen binding site of IgG, with Fc-III (Patent Literature 2). Dias et al. produced FcBP-2 by introducing further circularization into this cyclic peptide Fc-III by using Pro residues in the D- and L-forms and succeeded in increasing the affinity of Fc-III: KD=185 nM) for IgG up to KD=2 nM (Non Patent Literature 4).

Fassina et al. performed screening of a synthetic tetrapolypeptide library represented by (Arg Thr Xaa)4 Lys2 Lys Gly having a branched structure due to the Lys residue to produce a protein A mimetic (PAM) peptide competing with protein A (Non Patent Literature 5). It was demonstrated that TG19318, which is one of PAM peptides, has affinity of KD=300 nM for rabbit IgG and further that IgG contained in serum of a human, a bovine, a horse, a pig, a mouse, a rat, a goat, or a sheep can be purified by affinity chromatography using immobilized TG19318 (Non Patent Literature 6).

Ehrlich et al. used a phage library displaying linear peptides of 7 or 12 residues on filamentous bacteriophage M13 to isolate a peptide having affinity for a pFc' fragment obtained by pepsin digestion of humanized IgG (Non Patent Literature 7), as in the method of Suzuki et al.

Krook et al. used a phage library displaying linear peptides of 10-residue length on filamentous bacteriophage M13 to produce a peptide having affinity for the Fc region of human IgG. They confirmed by ELISA that this peptide had high affinity for IgG derived from a human or a pig (Non Patent Literature 8).

Verdoliva et al. performed screening of a synthetic peptide library represented by (Cys Xaa3)2 Lys Gly into which a branched structure due to the Lys residue and circularization due to the Cys residue are introduced, for mouse monoclonal IgG to produce peptide FcRM having affinity for the vicinity of the hinge region. They further reported construction of affinity chromatography on which this FcRM was immobilized to purify mouse or human derived IgG (Non Patent Literature 9).

Watanabe et al. used an artificial protein library including 10-residue microprotein chignolin and random amino acid sequences (Patent Literature 3) for increasing the affinity of a linear peptide, which shows low affinity for the Fc region of human IgG, to improve the affinity by 40,600 times without having a cyclic structure and produced a 54-residue polypeptide AF.p17 having a high affinity of KD=1.6 nM (Patent Literature 4 and Non Patent Literature 10).

Sakamoto et al. used a phage library displaying cyclic peptides represented by Cys Xaa7-10 Cys on T7 bacteriophage to produce a peptide having affinity for the Fc region of human IgG (Non Patent Literature 11). The peptide produced by them differs from the above-mentioned IgG affinity peptides produced so far in that the peptide recognizes an Fc region forming a non-native three-dimensional structure caused by acid treatment, not an Fc region having a native three-dimensional structure. Ito et al. disclosed that this peptide can be used to investigate the contents of non-native three-dimensional structures generated by acid treatment included in human antibody drugs, immunoglobulin preparations, and IgG reagents (Patent Literature 5).

Watanabe et al. used an artificial protein library including 10-residue microprotein chignolin (Patent Literature 3) to produce 25-residue artificial protein AF.2A1 having affinity for the Fc region of human IgG (Non Patent Literature 12). AF.2A1 had high specific affinity for the Fc region forming a non-native three-dimensional structure occurring by, for example, acid treatment, heat treatment, or reducing agent treatment and strictly distinguished between the native three-dimensional structure and the non-native three-dimensional structure of the Fc region (Patent Literature 4).

As described above, multiple IgG affinity peptides have been developed, but the molecular diversity thereof is not sufficient. This is because IgG is constituted as a heterotetramer composed of heavy chains each constituted of four domains VH, CH1, CH2, and CH3 and light chains each constituted of two domains VL and CL and thus has a complex structure constituted of six domains in total. In implementation of, for example, detection, purification, immobilization, analysis, or removal of antibodies or the like, antibody affinity molecules having characteristics suitable for respective use situations are necessary. Specifically, the antibody affinity molecules needed are those having appropriate characteristics in terms of, for example, the site of an antibody or a protein including an antibody domain to which the molecule binds, the degree of the specificity of molecular recognition, the ability to distinguish differences not only in amino acid sequences but also in changed three-dimensional structures, the degree of strength of the affinity, the ability to control binding/dissociation by, for example, a change in solution conditions, the solubility and stability, and the possibility of mass production.

Along with the expansion of the antibody drugs market, further sophistication of analytical techniques and separation/purification techniques targeting antibody molecules has been highly desired.

With regard to the analytical techniques, as techniques strongly desired for future advancement, particularly expected are development in three areas: (1) an analytical technique on molecular heterogeneity accompanying post-translational modifications including glycosylation, (2) an analytical technique on molecular heterogeneity accompanying a change in the three-dimensional structure of an antibody, and (3) an analytical technique on molecular heterogeneity accompanying formation of associate/aggregate (Non Patent Literature 13). It has been reported that antibody molecules form a non-native three-dimensional structure, called alternatively folded state (AFS), different from the usual native three-dimensional structure by various physical or chemical stresses (Non Patent Literatures 14 and 15). Such a non-native three-dimensional structure not only results in loss of activity of the antibody but also may cause protein aggregation. As a result, not only a reduction in drug efficacy but also risks that cause side effects due to induction of immunogenicity are suggested (Non Patent Literature 16), and the analytical technique on the non-native three-dimensional structures of antibodies is required to develop as an indispensable technique for quality control of antibody drugs (Non Patent Literature 17).

Examples of the analytical technique that can reveal the molecular shape or three-dimensional structure of a protein include X-ray crystal structure analysis, nuclear magnetic resonance, electron microscope, analytical ultracentrifugation, isoelectric focusing electrophoresis, dynamic light scattering, circular dichroism spectrum, and liquid chromatography (Non Patent Literature 17). Although the analytical techniques have respective advantages such as analysis accuracy, high throughput of measurement, and detection sensitivity, in general, analysis accuracy and throughput are in a trade-off relationship, and no spectroscopic and chromatographic methods satisfy both requirements. For example, X-ray crystal structure analysis and nuclear magnetic resonance, which can provide information on three-dimensional structure with atomic-level precision, need analysis time on the order of several months. In contrast, dynamic light scattering and liquid chromatography, which can complete the measurement in a few minutes, cannot detect a minute change in the molecular structure and trace incorporation. Accordingly, it is required to solve the problems related to compatibility between analysis accuracy and throughput of the analytical techniques.

On the other hand, as an antibody separation/purification technique, an affinity chromatography technique using a molecule having specific affinity for an antibody as a binding ligand is used. As the binding ligand for this application, natural proteins derived from bacteria, such as protein A and protein G, or artificially produced antibody affinity molecules are used. Although it is possible to bind/collect antibodies by these affinity molecules, most of the molecules have affinity for the native three-dimensional structure or non-native three-dimensional structure of the antibody Fc region (Patent Literatures 1 to 5 and Non Patent Literatures 3 to 12), and cannot specifically distinguish between the native three-dimensional structure and the non-native three-dimensional structure of the CH1-CL domain, which is the constant region of an antibody Fab region.

CITATION LIST

Patent Literature

Patent Literature 1: Japanese Unexamined Patent Application Publication No. 2004-187563
Patent Literature 2: International Publication No. WO2001/045746
Patent Literature 3: International Publication No. WO2014/103203
Patent Literature 4: International Publication No. WO2014/115229
Patent Literature 5: International Publication No. WO2008/054030
Patent Literature 6: Japanese Unexamined Patent Application Publication (Translation of PCT Application) No. 2011-517690

Non Patent Literature

Non Patent Literature 1: "Preclinical Development of Monoclonal Antibodies and Related Biologicals: Emerging technologies and new therapeutic candidates", pp. 16-20. Business Insights Ltd. (2010)
Non Patent Literature 2: Nelson A. L., (2010), Antibody fragments: hope and hype. MAbs. 2 (1), 77-83

Non Patent Literature 3: DeLano W. L., Ultsch M. H., de Vos A. M., and Wells J. A., (2000), Convergent solutions to binding at a protein-protein interface, Science, 287 (5456), 1279-1283

Non Patent Literature 4: Dias R. L., Fasan R., Moehle K., Renard A., Obrecht D., and Robinson J. A., (2006), Protein ligand design: from phage display to synthetic protein epitope mimetics in human antibody Fc-binding peptidomimetics, J. Am. Chem. Soc., 128 (8), 2726-2732

Non Patent Literature 5: Fassina G., Verdoliva A., Odierna M. R., Ruvo M., and Cassini G., (1996), Protein A mimetic peptide ligand for affinity purification of antibodies, J. Mol. Recognit., 9 (5-6), 564-569

Non Patent Literature 6: Fassina G., Verdoliva A., Palombo G., Ruvo M., and Cassani G., (1998), Immunoglobulin specificity of TG19318: a novel synthetic ligand for antibody affinity purification, J. Mol. Recognit., 11 (1-6), 128-133

Non Patent Literature 7: Ehrlich G. K. and Bailon P., (1998), Identification of peptides that bind to the constant region of a humanized IgG1 monoclonal antibody using phage display, J. Mol. Recognit., 11 (1-6), 121-125

Non Patent Literature 8: Krook M., Mosbach K., and Ramstrom O., (1998), Novel peptides binding to the Fc-portion of immunoglobulins obtained from a combinatorial phage display peptide library, J. Immunol. Methods., 221 (1-2), 151-157

Non Patent Literature 9: Verdoliva A., Marasco D., De Capua A., Saporito A., Bellofiore P., Manfredi V., Fattorusso R., Pedone C., and Ruvo M., (2005), A new ligand for immunoglobulin g subdomains by screening of a synthetic peptide library, Chembiochem., 6 (7), 1242-1253

Non Patent Literature 10: Watanabe H. and Honda S., (2015), Adaptive Assembly: Maximizing the Potential of a Given Functional Peptide with a Tailor-Made Protein Scaffold, Chem. Biol., 22 (9), 1165-1173

Non Patent Literature 11: Sakamoto K., Ito Y., Hatanaka T., Soni P. B., Mori T., and Sugimura K., (2009), Discovery and characterization of a peptide motif that specifically recognizes a non-native conformation of human IgG induced by acidic pH conditions, J. Biol. Chem., 284 (15), 9986-9993

Non Patent Literature 12: Watanabe H., Yamasaki K., and Honda S., (2014), Tracing primordial protein evolution through structurally guided stepwise segment elongation, J. Biol. Chem., 289 (6), 3394-3404

Non Patent Literature 13: Berkowitz S. A., Engen J. R., Mazzeo J. R., and Jones G. B., (2012), Analytical tools for characterizing biopharmaceuticals and the implications for biosimilars, Nat. Rev. Drug Discov., 11 (7), 527-540

Non Patent Literature 14: Buchner J., Renner M., Lilie H., Hinz H. J., Jaenicke R., Kiefhabel T., and Rudolph R., (1991), Alternatively folded states of an immunoglobulin, Biochemistry, 30 (28), 6922-6929

Non Patent Literature 15: Feige M. J., Simpson E. R., Herold E. M., Bepperling A., Heger K., and Buchner J., (2010), Dissecting the alternatively folded state of the antibody Fab fragment, J. Mol. Biol., 399 (5), 719-730

Non Patent Literature 16: Rosenberg A. S., (2006), Effects of protein aggregates an immunologic perspective, AAPS J., 8 (3), E501-507

Non Patent Literature 17: Beck A., Wagner-Rousset E., Ayoub D., Van Dors selaer A., and Sanglier-Cianferani S., (2013), Characterization of therapeutic antibodies and related products, Anal. Chem., 85 (2), 715-736

Non Patent Literature 18: Thies M. J., Kammermeier R., Richter K., and Buchner J., (2001), The alternatively folded state of the antibody C(H)3 domain, J. Mol. Biol., 309 (5), 1077-1085

Non Patent Literature 19: Huyghues-Despointes B. M. (1), Pace C. N., Englander S. W., and Scholtz J. M., (2001), Measuring the conformational stability of a protein by hydrogen exchange, Methods Mol. Biol., 168, 69-92

Non Patent Literature 20: Kanmert D., Brorsson A. C., Jonsson B. H., and Enander K., (2011), Thermal induction of an alternatively folded state in human IgG-Fc, Biochemistry, 50 (6), 981-988

Non Patent Literature 21: Luo Q., Joubert M. K., Stevenson R., Ketchem R. R., Narhi L. O., and Wypych J., (2011), Chemical modifications in therapeutic protein aggregates generated under different stress conditions, J. Biol. Chem., 286 (28), 25134-25144

Non Patent Literature 22: Joubert M. K., Hokom M., Eakin C., Zhou L., Deshpande M., Baker M. P., Goletz T. J., Kerwin B. A., Chirmule N., Narhi L. O., and Jawa V., (2012), Highly aggregated antibody therapeutics can enhance the in vitro innate and late-stage T-cell immune responses, J. Biol. Chem., 287 (30), 25266-25279

Non Patent Literature 23: Basle E., Joubert N., and Pucheault M., (2010), Protein chemical modification on endogenous amino acids, Chem. Biol., 17 (3), 213-227

Non Patent Literature 24: Kanno S., Yanagida Y., Haruyama T., Kobatake E., and Aizawa M., (2000), Assembling of engineered IgG-binding protein on gold surface for highly oriented antibody immobilization, J. Biotechnol., 76 (2-3), 207-214

Non Patent Literature 25: Hober S., Nord K., and Linhult M., (2007), Protein A chromatography for antibody purification, J. Chromatogr. B Analyt. Technol. Biomed. Life Sci., 848 (1), 40-47

Non Patent Literature 26: Amblard M., Fehrentz J. A., Martinez J., and Subra G., (2005), Fundamentals of modern peptide synthesis, Methods Mol. Biol., 298, 3-24

Non Patent Literature 27: Lee J. H. (1), Kim J. H., Hwang S. W., Lee W. J., Yoon H. K., Lee H. S., and Hong S. S., (2000), High-level expression of antimicrobial peptide mediated by a fusion partner reinforcing formation of inclusion bodies, Biochem. Biophys. Res. Commun., 277 (3), 575-580

Non Patent Literature 28: "Label-Free Biosensor Methods in Drug Discovery", pp. 35-76. Springer (2015)

Non Patent Literature 29: Puckett M. C., (2015), Hexahistidine (6xHis) fusion-based assays for protein-protein interactions, Methods Mol. Biol., 1278, 365-370

Non Patent Literature 30: Wittig I. and Schagger H., (2009), Native electrophoretic techniques to identify protein-protein interactions, Proteomics., 9 (23), 5214-5223

Non Patent Literature 31: Raines R. T., (2015), Fluorescence polarization assay to quantify protein-protein interactions: an update, Methods Mol. Biol., 1278, 323-327

Non Patent Literature 32: Yageta S., Lauer T. M., Trout B. L., and Honda S., (2015), Conformational and Colloidal Stabilities of Isolated Constant Domains of Human Immunoglobulin G and Their Impact on Antibody Aggregation under Acidic Conditions, Mol. Pharm., 12 (5), 1443-1455

Non Patent Literature 33: Khan F. et al., (2006), Double-Hexahistidine Tag with High-Affinity Binding for Protein Immobilization, Purification, and Detection on Ni-Nitrilotriacetic Acid Surfaces, Anal. Chem., 78, 3072-3079

Non Patent Literature 34: Silverman, J. et al., (2005), Multivalent avimer proteins evolved by exon shuffling of a family of human receptor domains, Nat. Biotechnol., 23, 1556-1561

Non Patent Literature 35: Bell M. R. et al., (2013), To fuse or not to fuse: What is your purpose? Protein Sci., 22, 1466-1477

Non Patent Literature 36: Gerdes H. H. et al., (1996), Green Fluorescent Protein: Applications in Cell Biology, FEBS Lett., 389, 44-47

Non Patent Literature 37: Uhlen M. et al., (1992), Fusion proteins in biotechnology, Curr. Opin. Biotechnol., 3, 363-369

Non Patent Literature 38: Nilsson J. et al., (1994), Competitive elution of protein A fusion proteins allows specific recovery under mild conditions, Eur. J. Biochem., 224, 103-108

SUMMARY OF INVENTION

Technical Problem

It is an object of the present invention to provide a novel polypeptide that has specific affinity for a protein partially including a CH1-CL domain forming a non-native three-dimensional structure among proteins including a CH1-CL domain of an antibody such as IgG or a Fab region and can be suitably used in detection, immobilization, or removal of the protein, to expand the molecular diversity of an affinity polypeptide that can be used in industry, such as antibody research, production, and quality control, and thereby expand the diversity of detection, immobilization, or removal of the protein.

Solution to Problem

The present inventors have diligently studied to solve the above problems and as a result, have found that a short polypeptide having a specific amino acid sequence pattern has specific affinity for a CH1-CL domain forming a non-native three-dimensional structure. The present invention has been accomplished based on these findings. In the present specification, the terms "peptide", "polypeptide", and "protein" are used interchangeably.

That is, the present invention encompasses the followings:

[1] A polypeptide consisting of an amino acid sequence represented by Formula 1:

(1)
(SEQ ID NO: 1)
P-Q-x-I-x-L-x-[IL]-[NT]-[YW]

(wherein x represents an amino acid residue, and brackets ([ ]) represent any one of the amino acid residues within the brackets) or a polypeptide consisting of an amino acid sequence having addition of one or several amino acid residues in the amino acid sequence represented by Formula 1, wherein the polypeptide has affinity for the CH1-CL domain of immunoglobulin G. The "several" amino acid residues to be added mean, for example, 1 to 20, preferably 1 to 10, and more preferably 1 to 5 amino acid residues, unless otherwise specified.

In above [1], the polypeptide may be a polypeptide consisting of an amino acid sequence represented by P-Q-[DNEQHFYW]-I-[RKHSTY]-L-[GAVLIPSTY]-[IL]-[NT]-[YW] (wherein brackets represent any one of the amino acid residues within the brackets) or a polypeptide consisting of an amino acid sequence having addition of one or several amino acid residues in the amino acid sequence represented by the formula, wherein the polypeptide has affinity for a CH1-CL domain of immunoglobulin G.

In above [1], the polypeptide may be a polypeptide consisting of an amino acid sequence represented by P-Q-[EW]-I-[RT]-L-[IT]-[IL]-[NT]-[YW] (wherein brackets represent any one of the amino acid residues within the brackets) according to Formula 1 or a polypeptide consisting of an amino acid sequence having addition of one or several amino acid residues in the amino acid sequence represented by the formula, wherein the polypeptide has affinity for a CH1-CL domain of immunoglobulin G.

[2] The polypeptide according to above [1], wherein the polypeptide is a polypeptide consisting of an amino acid sequence represented by SEQ ID NO: 2 or 3:

(SEQ ID NO: 2)
PQEIRLILNW, (SEQ ID NO: 3)
PQWITLTITY, or a polypeptide consisting of an amino acid sequence having addition, deletion, substitution, or insertion of one amino acid residue in the amino acid sequence represented by SEQ ID NO: 2 or 3 by, wherein the polypeptide has affinity for a CH1-CL domain of immunoglobulin G. The substitution of the amino acid residue is preferably conservative amino acid substitution.

[3] A polypeptide consisting of an amino acid sequence represented by Formula 2:

(2)
(SEQ ID NO: 4)
Y-D-P-E-T-G-T-W-P-Q-x-I-x-L-x-[IL]-[NT]-[YW]

(wherein x represents an amino acid residue, and brackets represent any one of the amino acid residues within the brackets) or a polypeptide consisting of an amino acid sequence having addition of one or several amino acid residues in the amino acid sequence represented by Formula 2, wherein the polypeptide has affinity for a CH1-CL domain of immunoglobulin G.

The polypeptide according to above [3] may be a polypeptide consisting of an amino acid sequence represented by Y-D-P-E-T-G-T-W-P-Q-[DNEQHFYW]-I-[RKHSTY]-L-[GAVLIPSTY]-[IL]-[NT]-[YW] (wherein brackets represent any one of the amino acid residues within the brackets) or a polypeptide consisting of an amino acid sequence having addition of one or several amino acid residues in the amino acid sequence the formula, wherein the polypeptide has affinity for a CH1-CL domain of immunoglobulin G.

In above [3], the polypeptide may be a polypeptide consisting of an amino acid sequence represented by Y-D-P-E-T-G-T-W-P-Q-[EW]-I-[RT]-L-[IT]-[IL]-[NT]-[YW] (wherein brackets represent any one of the amino acid residues within the brackets) or a polypeptide consisting of an amino acid sequence having addition of one or several amino acid residues in the amino acid sequence represented by the formula, wherein the polypeptide has affinity for a CH1-CL domain of immunoglobulin G.

[4] The polypeptide according to [3], wherein the polypeptide is a polypeptide consisting of an amino acid sequence represented by any one of SEQ ID NOs: 5, 6, and 36 to 41:

```
                                          (SEQ ID NO: 5)
YDPETGTWPQEIRLILNW (SEQ ID NO: 6)
YDPETGTWPQWITLTITY (SEQ ID NO: 36)
HNFTLPLWMYYDPETGTWPQEIRLILNW (SEQ ID NO: 37)
RFPLMFGPSWYDPETGTWPQEIRLILNW (SEQ ID NO: 38)
RFYVLLDSSWYDPETGTWPQEIRLILNW (SEQ ID NO: 39)
VSKFYPLWTRYDPETGTWPQEIRLILNW (SEQ ID NO: 40)
VFLVLMGPEFYDPETGTWPQEIRLILNW (SEQ ID NO: 41)
FLLFCPRSLCYDPETGTWPQEIRLILNW
``` or a polypeptide consisting of an amino acid sequence having addition, deletion, substitution, or insertion of one or two amino acid residues in the amino acid sequence represented by any one of SEQ ID NOs: 5, 6, and 36 to 41, wherein the polypeptide has affinity for a CH1-CL domain of immunoglobulin G. The substitution of the amino acid residue(s) is preferably conservative amino acid substitution.

[5] A polypeptide consisting of an amino acid sequence represented by Formula 3:

```
                                          (SEQ ID NO: 7)
P-N-S-G-G-G-G-S-Y-D-P-E-T-G-T-W-P-Q-x-I-
x-L-x-[IL]-[NT]-[YW]
```

(wherein x represents an amino acid residue, and brackets represent any one of the amino acid residues within the brackets) or a polypeptide consisting of an amino acid sequence having one or several amino acid residues in the amino acid sequence represented by Formula 3, wherein the polypeptide has affinity for a CH1-CL domain of immunoglobulin G.

In above [5], the polypeptide may be a polypeptide consisting of an amino acid sequence represented by P-N-S-G-G-G-G-S-Y-D-P-E-T-G-T-W-P-Q-[DNEQHFYW]-1-[RKHSTY]-L-[GAVLIPSTY]-[IL]-[NT]-[YW] (wherein brackets represent any one of the amino acid residues within the brackets) or a polypeptide consisting of an amino acid sequence having addition of one or several amino acid residues in the amino acid sequence represented by the formula, wherein the polypeptide has affinity for a CH1-CL domain of immunoglobulin G.

In above [5], the polypeptide may be a polypeptide consisting of an amino acid sequence represented by P-N-S-G-G-G-G-S-Y-D-P-E-T-G-T-W-P-Q-[EW]-I-[RT]-L-[IT]-[IL]-[NT]-[YW] (wherein brackets represent any one of the amino acid residues within the brackets) or a polypeptide consisting of an amino acid sequence having addition of one or several amino acid residues in the amino acid sequence represented by the formula, wherein the polypeptide has affinity for a CH1-CL domain of immunoglobulin G. The meaning of "several" can be the same as that in above [1] (see the explanation below).

[6] The polypeptide according to [5], wherein the polypeptide is a polypeptide consisting of an amino acid sequence represented by any one of SEQ ID NOs: 8 to 912:

```
                                          (SEQ ID NO: 8)
PNSGGGGSYDPETGTWPQEIRLILNW (SEQ ID NO: 9)
PNSGGGGSYDPETGTWPQWITLTITY (SEQ ID NO: 10)
PNSGGGGSYDPETGTWAQEIRLILNW (SEQ ID NO: 11)
PNSGGGGSYDPETGTWPAEIRLILNW (SEQ ID NO: 12)
PNSGGGGSYDPETGTWPQEIRLIANW
``` or a polypeptide consisting of an amino acid sequence having addition, deletion, substitution, or insertion of one to three amino acid residues in the amino acid sequence represented by any one of SEQ ID NOs: 8 to 12, wherein the polypeptide has affinity for a CH1-CL domain of immunoglobulin G. The substitution of the amino acid residue(s) is preferably conservative amino acid substitution.

[7] A tandem polypeptide having the polypeptide according to any one of [1] to [6] with a second polypeptide at the amino-terminus, the carboxyl-terminus, or both termini thereof, wherein the tandem polypeptide has affinity for a CH1-CL domain of immunoglobulin G.

[8] A fusion protein having a protein bound to the amino-terminus, the carboxy-terminus, or both termini of the polypeptide according to any one of [1] to [6], wherein the fusion protein has affinity for a CH1-CL domain of immunoglobulin G.

The protein according to [8], consisting of an amino acid sequence represented by any one of SEQ ID NOs: 13 to 15 and 42 to 46:

```
                                         (SEQ ID NO: 13)
MSDKIIHLTDDSFDTDVLKADGAILVDFWAEWCGPCKMIAPILDEIAD

EYQGKLTVAKLNIDQNPGTAPKYGIRGIPTLLLFKNGEVAATKVGALS

KGQLKEFLDANLAGSGSGHTSGGGGSNNNPPTPTPSSGSGHHHHHHSA

ALEVLFQGPGYQDPNSGGGGSYDPETGTWPQAQKKEIQT (SEQ ID NO: 14)
MSDKIIHLTDDSFDTDVLKADGAILVDFWAEWCGPCKMIAPILDEIAD

EYQGKLTVAKLNIDQNPGTAPKYGIRGIPTLLLFKNGEVAATKVGALS

KGQLKEFLDANLAGSGSGHTSGGGGSNNNPPTPTPSSGSGHHHHHHSA

ALEVLFQGPGYQDPNSGGGGSYDPETGTWPQEIRLILNW (SEQ ID NO: 15)
MSDKIIHLTDDSFDTDVLKADGAILVDFWAEWCGPCKMIAPILDEIAD

EYQGKLTVAKLNIDQNPGTAPKYGIRGIPTLLLFKNGEVAATKVGALS

KGQLKEFLDANLAGSGSGHTSGGGGSNNNPPTPTPSSGSGHHHHHHSA

ALEVLFQGPGYQDPNSGGGGSYDPETGTWPQWITLTITY (SEQ ID NO: 42)
MSDKIIHLTDDSFDTDVLKADGAILVDFWAEWCGPCKMIAPILDEIAD

EYQGKLTVAKLNIDQNPGTAPKYGIRGIPTLLLFKNGEVAATKVGALS

KGQLKEFLDANLAGSGSGHTSGGGGSNNNPPTPTPSSGSGHHHHHHSA

ALEVLFQGPGYQDPNSGGGGSHNFTLPLWMYYDPETGTWPQEIRLILN

W
```

(SEQ ID NO: 43)
MSDKIIHLTDDSFDTDVLKADGAILVDFWAEWCGPCKMIAPILDEIAD
EYQGKLTVAKLNIDQNPGTAPKYGIRGIPTLLLFKNGEVAATKVGALS
KGQLKEFLDANLAGSGSGHTSGGGGSNNNPPTPTPSSGSGHHHHHHSA
ALEVLFQGPGYQDPNSGGGGSRFPLMFGPSWYDPETGTWPQEIRLILN
W (SEQ ID NO: 44)
MSDKIIHLTDDSFDTDVLKADGAILVDFWAEWCGPCKMIAPILDEIAD
EYQGKLTVAKLNIDQNPGTAPKYGIRGIPTLLLFKNGEVAATKVGALS
KGQLKEFLDANLAGSGSGHTSGGGGSNNNPPTPTPSSGSGHHHHHHSA
ALEVLFQGPGYQDPNSGGGGSRFYVLLDSSWYDPETGTWPQEIRLILN
W (SEQ ID NO: 45)
MSDKIIHLTDDSFDTDVLKADGAILVDFWAEWCGPCKMIAPILDEIAD
EYQGKLTVAKLNIDQNPGTAPKYGIRGIPTLLLFKNGEVAATKVGALS
KGQLKEFLDANLAGSGSGHTSGGGGSNNNPPTPTPSSGSGHHHHHHSA
ALEVLFQGPGYQDPNSGGGGSVSKFYPLWTRYDPETGTWPQEIRLILN
W (SEQ ID NO: 46)
MSDKIIHLTDDSFDTDVLKADGAILVDFWAEWCGPCKMIAPILDEIAD
EYQGKLTVAKLNIDQNPGTAPKYGIRGIPTLLLFKNGEVAATKVGALS
KGQLKEFLDANLAGSGSGHTSGGGGSNNNPPTPTPSSGSGHHHHHHSA
ALEVLFQGPGYQDPNSGGGGSVFLVLMGPEFYDPETGTWPQEIRLILN
W.

[10] A nucleic acid encoding the polypeptide according to any one of [1] to [7] or the protein according to [8] or [9].

[11] The nucleic acid according to [10], consisting of a nucleotide sequence represented by any one of SEQ ID NOs: 16 to 18 and 47 to 51:

(SEQ ID NO: 16)
ATGAGCGATAAAATTATTCACCTGACTGACGACAGTTTTGACACGGAT
GTACTCAAAGCGGACGGGGCGATCCTCGTCGATTTCTGGGCAGAGTGG
TGCGGTCCGTGCAAAATGATCGCCCCGATTCTGGATGAAATCGCTGAC
GAATATCAGGGCAAACTGACCGTTGCAAAACTGAACATCGATCAAAAC
CCTGGCACTGCGCCGAAATATGGCATCCGTGGTATCCCGACTCTGCTG
CTGTTCAAAAACGGTGAAGTGGCGGCAACCAAAGTGGGTGCACTGTCT
AAAGGTCAGTTGAAAGAGTTCCTCGACGCTAACCTGGCCGGTTCTGGT
TCTGGCCATACTAGTGGTGGTGGCGGTTCTAATAACAATCCTCCTACT
CCTACTCCATCTAGTGGTTCTGGTCATCACCATCACCATCACTCCGCG
GCTCTTGAAGTCCTCTTTCAGGGACCCGGGTACCAGGATCCGAATTCG
GGAGGAGGGGGATCATACGACCCCGAGACGGGCACGTGGCCACAAGCA
CAGAAAAAAGAGATACAAACA (SEQ ID NO: 17)
ATGAGCGATAAAATTATTCACCTGACTGACGACAGTTTTGACACGGAT
GTACTCAAAGCGGACGGGGCGATCCTCGTCGATTTCTGGGCAGAGTGG
TGCGGTCCGTGCAAAATGATCGCCCCGATTCTGGATGAAATCGCTGAC
GAATATCAGGGCAAACTGACCGTTGCAAAACTGAACATCGATCAAAAC
CCTGGCACTGCGCCGAAATATGGCATCCGTGGTATCCCGACTCTGCTG
CTGTTCAAAAACGGTGAAGTGGCGGCAACCAAAGTGGGTGCACTGTCT
AAAGGTCAGTTGAAAGAGTTCCTCGACGCTAACCTGGCCGGTTCTGGT
TCTGGCCATACTAGTGGTGGTGGCGGTTCTAATAACAATCCTCCTACT
CCTACTCCATCTAGTGGTTCTGGTCATCACCATCACCATCACTCCGCG
GCTCTTGAAGTCCTCTTTCAGGGACCCGGGTACCAGGATCCGAATTCG
GGAGGAGGGGGATCATACGACCCCGAGACGGGCACGTGGCCACAGGAA
ATTAGACTAATACTTAATTGG (SEQ ID NO: 18)
ATGAGCGATAAAATTATTCACCTGACTGACGACAGTTTTGACACGGAT
GTACTCAAAGCGGACGGGGCGATCCTCGTCGATTTCTGGGCAGAGTGG
TGCGGTCCGTGCAAAATGATCGCCCCGATTCTGGATGAAATCGCTGAC
GAATATCAGGGCAAACTGACCGTTGCAAAACTGAACATCGATCAAAAC
CCTGGCACTGCGCCGAAATATGGCATCCGTGGTATCCCGACTCTGCTG
CTGTTCAAAAACGGTGAAGTGGCGGCAACCAAAGTGGGTGCACTGTCT
AAAGGTCAGTTGAAAGAGTTCCTCGACGCTAACCTGGCCGGTTCTGGT
TCTGGCCATACTAGTGGTGGTGGCGGTTCTAATAACAATCCTCCTACT
CCTACTCCATCTAGTGGTTCTGGTCATCACCATCACCATCACTCCGCG
GCTCTTGAAGTCCTCTTTCAGGGACCCGGGTACCAGGATCCGAATTCG
GGAGGAGGGGGATCATACGACCCCGAGACGGGCACGTGGCCGCAGTGG
ATAACTCTTACGATAACGTAT (SEQ ID NO: 47)
ATGAGCGATAAAATTATTCACCTGACTGACGACAGTTTTGACACGGAT
GTACTCAAAGCGGACGGGGCGATCCTCGTCGATTTCTGGGCAGAGTGG
TGCGGTCCGTGCAAAATGATCGCCCCGATTCTGGATGAAATCGCTGAC
GAATATCAGGGCAAACTGACCGTTGCAAAACTGAACATCGATCAAAAC
CCTGGCACTGCGCCGAAATATGGCATCCGTGGTATCCCGACTCTGCTG
CTGTTCAAAAACGGTGAAGTGGCGGCAACCAAAGTGGGTGCACTGTCT
AAAGGTCAGTTGAAAGAGTTCCTCGACGCTAACCTGGCCGGTTCTGGT
TCTGGCCATACTAGTGGTGGTGGCGGTTCTAATAACAATCCTCCTACT
CCTACTCCATCTAGTGGTTCTGGTCATCACCATCACCATCACTCCGCG
GCTCTTGAAGTCCTCTTTCAGGGACCCGGGTACCAGGATCCGAATTCG
GGAGGAGGGGGATCACATAATTTTACTCTTCCTCTGTGGATGTATTAC
GACCCCGAGACGGGCACGTGGCCGCAGGAAATTCGCCTGATTCTGAAC
TGG (SEQ ID NO: 48)
ATGAGCGATAAAATTATTCACCTGACTGACGACAGTTTTGACACGGAT
GTACTCAAAGCGGACGGGGCGATCCTCGTCGATTTCTGGGCAGAGTGG

TGCGGTCCGTGCAAAATGATCGCCCCGATTCTGGATGAAATCGCTGAC

GAATATCAGGGCAAACTGACCGTTGCAAAACTGAACATCGATCAAAAC

CCTGGCACTGCGCCGAAATATGGCATCCGTGGTATCCCGACTCTGCTG

CTGTTCAAAAACGGTGAAGTGGCGGCAACCAAAGTGGGTGCACTGTCT

AAAGGTCAGTTGAAAGAGTTCCTCGACGCTAACCTGGCCGGTTCTGGT

TCTGGCCATACTAGTGGTGGTGGCGGTTCTAATAACAATCCTCCTACT

CCTACTCCATCTAGTGGTTCTGGTCATCACCATCACCATCACTCCGCG

GCTCTTGAAGTCCTCTTTCAGGGACCCGGGTACCAGGATCCGAATTCG

GGAGGAGGGGGATCACGTTTTCCGTTGATGTTTGGGCCGTCTTGGTAC

GACCCCGAGACGGGCACGTGGCCGCAGGAAATTCGCCTGATTCTGAAC

TGG (SEQ ID NO: 49)
ATGAGCGATAAAATTATTCACCTGACTGACGACAGTTTTGACACGGAT

GTACTCAAAGCGGACGGGGCGATCCTCGTCGATTTCTGGGCAGAGTGG

TGCGGTCCGTGCAAAATGATCGCCCCGATTCTGGATGAAATCGCTGAC

GAATATCAGGGCAAACTGACCGTTGCAAAACTGAACATCGATCAAAAC

CCTGGCACTGCGCCGAAATATGGCATCCGTGGTATCCCGACTCTGCTG

CTGTTCAAAAACGGTGAAGTGGCGGCAACCAAAGTGGGTGCACTGTCT

AAAGGTCAGTTGAAAGAGTTCCTCGACGCTAACCTGGCCGGTTCTGGT

TCTGGCCATACTAGTGGTGGTGGCGGTTCTAATAACAATCCTCCTACT

CCTACTCCATCTAGTGGTTCTGGTCATCACCATCACCATCACTCCGCG

GCTCTTGAAGTCCTCTTTCAGGGACCCGGGTACCAGGATCCGAATTCG

GGAGGAGGGGGATCACGGTTTTATGTTCTGCTGGATTCTTCTTGGTAC

GACCCCGAGACGGGCACGTGGCCGCAGGAAATTCGCCTGATTCTGAAC

TGG (SEQ ID NO: 50)
ATGAGCGATAAAATTATTCACCTGACTGACGACAGTTTTGACACGGAT

GTACTCAAAGCGGACGGGGCGATCCTCGTCGATTTCTGGGCAGAGTGG

TGCGGTCCGTGCAAAATGATCGCCCCGATTCTGGATGAAATCGCTGAC

GAATATCAGGGCAAACTGACCGTTGCAAAACTGAACATCGATCAAAAC

CCTGGCACTGCGCCGAAATATGGCATCCGTGGTATCCCGACTCTGCTG

CTGTTCAAAAACGGTGAAGTGGCGGCAACCAAAGTGGGTGCACTGTCT

AAAGGTCAGTTGAAAGAGTTCCTCGACGCTAACCTGGCCGGTTCTGGT

TCTGGCCATACTAGTGGTGGTGGCGGTTCTAATAACAATCCTCCTACT

CCTACTCCATCTAGTGGTTCTGGTCATCACCATCACCATCACTCCGCG

GCTCTTGAAGTCCTCTTTCAGGGACCCGGGTACCAGGATCCGAATTCG

GGAGGAGGGGGATCAGTGAGTAAGTTTTATCCGCTGTGGACGCGGTAC

GACCCCGAGACGGGCACGTGGCCGCAGGAAATTCGCCTGATTCTGAAC

TGG (SEQ ID NO: 51)
ATGAGCGATAAAATTATTCACCTGACTGACGACAGTTTTGACACGGAT

GTACTCAAAGCGGACGGGGCGATCCTCGTCGATTTCTGGGCAGAGTGG

TGCGGTCCGTGCAAAATGATCGCCCCGATTCTGGATGAAATCGCTGAC

GAATATCAGGGCAAACTGACCGTTGCAAAACTGAACATCGATCAAAAC

CCTGGCACTGCGCCGAAATATGGCATCCGTGGTATCCCGACTCTGCTG

CTGTTCAAAAACGGTGAAGTGGCGGCAACCAAAGTGGGTGCACTGTCT

AAAGGTCAGTTGAAAGAGTTCCTCGACGCTAACCTGGCCGGTTCTGGT

TCTGGCCATACTAGTGGTGGTGGCGGTTCTAATAACAATCCTCCTACT

CCTACTCCATCTAGTGGTTCTGGTCATCACCATCACCATCACTCCGCG

GCTCTTGAAGTCCTCTTTCAGGGACCCGGGTACCAGGATCCGAATTCG

GGAGGAGGGGGATCAGTGTTTCTTGTTTTGATGGGCCTGAGTTTTAC

GACCCCGAGACGGGCACGTGGCCGCAGGAAATTCGCCTGATTCTGAAC

TGG.

[12] A recombinant vector comprising the nucleic acid according to [10] or [11].

[13] A transformant into which the recombinant vector according to [12] is introduced.

[14] A recombinant phage or a recombinant virus comprising the nucleic acid according to [10] or [11].

[15] A modified polypeptide or a modified protein having the polypeptide according to any one of [1] to [7] or the protein according to [8] bound to an organic compound, or an inorganic compound, or both an organic compound and an inorganic compound, wherein the modified polypeptides or the modified protein has affinity for a CH1-CL domain of immunoglobulin G.

[16] An immobilized polypeptide or an immobilized protein, where the polypeptide according to any one of [1] to [7], the protein according to [8] or [9], or the polypeptide or the protein according to [15] is immobilized on a water-insoluble solid-phase support.

[17] A kit for detecting, purifying, immobilizing, or removing a protein partially including a CH1-CL domain of immunoglobulin G, the CH1-CL domain forming a non-native three-dimensional structure, the kit comprising at least one selected from the group consisting of the polypeptide according to any one of [1] to [7], the protein according to [8] or [9], the nucleic acid according to [10] or [11], the recombinant vector according to [12], the transformant according to [13], the recombinant phage or the recombinant virus according to [14], the polypeptide or the protein according to [15], and the immobilized polypeptide or the immobilized protein according to [16].

[18] A method for detecting a protein partially including a CH1-CL domain of immunoglobulin G, the CH1-CL domain forming a non-native three-dimensional structure, the method comprising:

(1) contacting a test sample to be contaminated with the protein including the CH1-CL domain, with the polypeptide according to any one of [1] to [7], the protein according to [8] or [9], the transformant according to [13], the recombinant phage or the recombinant virus according to [14], the polypeptide or the protein according to [15], or the immobilized polypeptide or the immobilized protein according to [16]; and (2) determining whether or not a bond is formed between the protein including the CH1-CL domain and the polypeptide, the protein, the transformant, the recombinant phage or the recombinant virus, or the immobilized polypeptide or the immobilized protein.

[19] A method for purifying a protein partially including a CH1-CL domain of immunoglobulin G, the CH1-CL domain forming a non-native three-dimensional structure, the method comprising:

(1) contacting a sample containing the protein including the CH1-CL domain with the polypeptide according to any one of [1] to [7], the protein according to [8] or [9], the transformant according to [13], the recombinant phage or the recombinant virus according to [14], the polypeptide or the protein according to [15], or the immobilized polypeptide or the immobilized protein according to [16] to bind the protein including the CH1-CL domain to the polypeptide, the protein, the transformant, the recombinant phage or the recombinant virus, or the immobilized polypeptide or the immobilized protein; and (2) collecting the protein including the CH1-CL domain bound to the polypeptide, the protein, the transformant, the recombinant phage or the recombinant virus, or the immobilized polypeptide or the immobilized protein from the sample.

[20] A method for removing a protein partially including a CH1-CL domain of immunoglobulin G, the CH1-CL domain forming a non-native three-dimensional structure, the method comprising:

(1) contacting a sample containing the protein including the CH1-CL domain with the polypeptide according to any one of [1] to [7], the protein according to [8] or [9], the transformant according to [13], the recombinant phage or the recombinant virus according to [14], the polypeptide or the protein according to [15], or the immobilized polypeptide or the immobilized protein according to [16] to bind the protein including the CH1-CL domain to the polypeptide, the protein, the transformant, the recombinant phage or the recombinant virus, or the immobilized polypeptide or the immobilized protein; and (2) removing the protein including the CH1-CL domain bound to the polypeptide, the protein, the transformant, the recombinant phage or the recombinant virus, or the immobilized polypeptide or the immobilized protein from the sample.

In substitution of an amino acid residue, it is desirable to replace the amino acid residue with another amino acid conserving the properties of the amino acid side chain. For example, based on the properties of amino acid side chains, the following classification has been established:

Hydrophobic amino acids (A, I, L, M, F, P, W, Y, and V),
Hydrophilic amino acids (R, D, N, C, E, Q, G, H, K, S, and T),
Amino acids having aliphatic side chains (G, A, V, L, I, and P),
Amino acids having hydroxyl group-containing side chains (S, T, and Y),
Amino acids having sulfur atom-containing side chains (C and M),
Amino acids having carboxylic acid and amide-containing side chains (D, N, E, and Q),
Amino acids having base-containing side chains (R, K, and H), and
Amino acids having aromatic-containing side chains (H, F, Y, and W),
(Any letter in parentheses represents an amino acid shown in one-letter notation).

It is already known that a polypeptide having an amino acid sequence modified by deletion, addition, and/or substitution of one or several amino acid residues in the amino acid sequence with other amino acids maintains the biological activity thereof (Mark, D. F. et al., Proc. Natl. Acad. Sci. USA, (1984), 81, 5662-5666; Zoller, M. J. and Smith, M., Nucleic Acids Research, (1982), 10, 6487-6500; Wang, A. et al., Science, 224, 1431-1433; Dalbadie-McFarland, G. et al., Proc. Natl. Acad. Sci. USA, (1982), 79, 6409-6413). That is, it is generally said that in the amino acid sequence constituting a certain polypeptide, amino acids classified into the same group are highly likely to maintain the activity of the polypeptide when substituted with each other. In the present invention, the substitution between amino acids of the same group in the above-mentioned amino acid groups is referred to as "conservative substitution" or "conservative amino acid substitution".

Advantageous Effects of Invention

The polypeptide of the present invention has specific affinity for a protein partially including a CH1-CL domain forming a non-native three-dimensional structure among proteins including a CH1-CL domain of an antibody such as IgG or a Fab region thereof. As a result, it is possible to distinguish between the non-native three-dimensional structure and the native three-dimensional structure of a CH1-CL domain. Alternatively, it is possible to detect or immobilize a protein partially including a CH1-CL domain forming a non-native three-dimensional structure by using the polypeptide of the present invention.

In addition, AF.ab9 (SEQ ID NO: 8), a polypeptide including the amino acid sequence represented by SEQ ID NO: 1 as a common sequence, can specifically distinguish between a Fab region partially including a CH1-CL domain forming a non-native three-dimensional structure and a Fab region not including the CH1-CL domain, and therefore can detect a change in the three-dimensional structure specific to the CH1-CL domain of IgG.

Furthermore, AF.ab9 (SEQ ID NO: 8), a polypeptide including the amino acid sequence represented by SEQ ID NO: 1 as a common sequence, changes the binding response to IgG treated with acid buffer solutions depending on the degrees of acidity of the buffer solutions, and therefore can detect the degree of change in the three-dimensional structure occurring depending on the degree of physical or chemical stress during manufacturing or storing the protein partially including a CH1-CL domain, such as IgG or a Fab region.

BRIEF DESCRIPTION OF DRAWINGS

FIG. 2-1 shows the results of evaluation, by surface plasmon resonance, of affinity between each of 32 clones of fusion proteins (5 and 2.5 μM) including an affinity polypeptide prepared as thioredoxin fusion protein and a CH1-CL domain forming a non-native three-dimensional structure and immobilized on a sensor chip. The vertical axis of each graph represents the magnitude (resonance unit) of the detection value, which reflects the weight of the molecules bonded to the sensor chip. The magnitude of the detection value depends on a plurality of measurement parameters such as the concentration and the flow rate of the specimen, but the magnitudes of the detection values when measured under the same conditions roughly correspond to the degrees of affinity of the specimens. (Incidentally, academically correct evaluation is actually possible by fitting a resulting experimental curve with a theoretical curve to calculate and compare, for example, the equilibrium dissociation constant, dissociation rate constant, and binding rate constants. The same applies to FIGS. 3 to 7.) The unit is the same between the graphs, and the same value means the same magnitude.

FIG. 2-2 is the continuation of FIG. 2-1.

DESCRIPTION OF EMBODIMENTS

Figure 1:
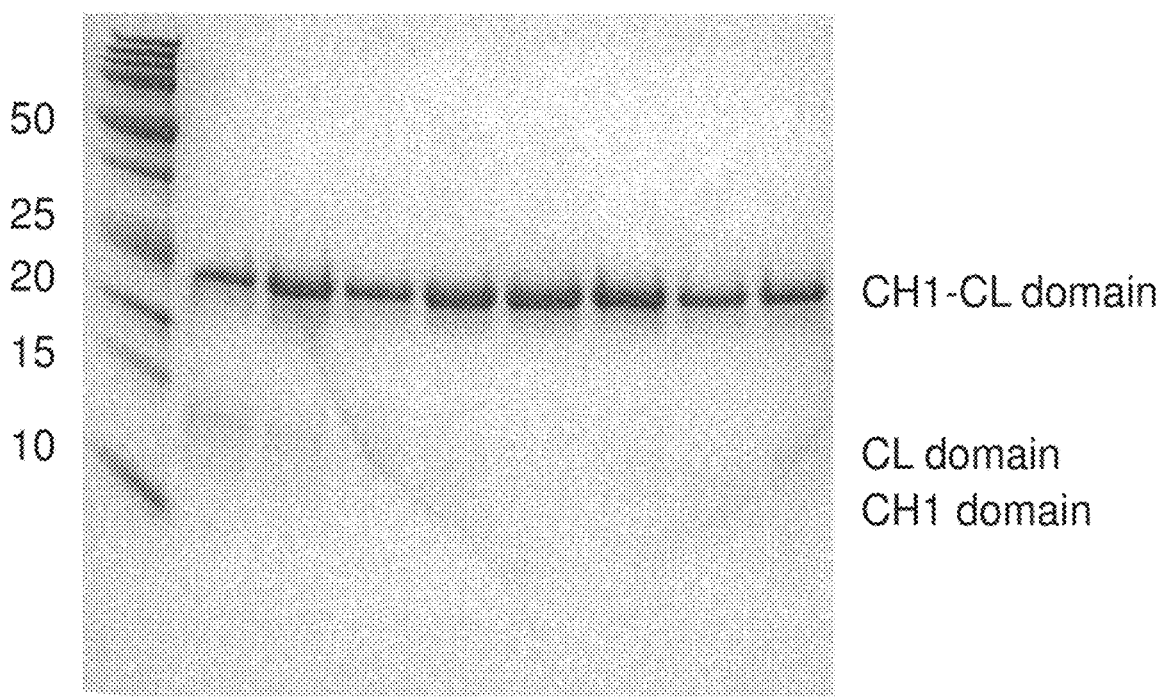
FIG. 1 shows the results of verification of the purity of a purified CH1-CL domain by sodium dodecyl sulfate (SDS) polyacrylamide gel electrophoresis under nonreducing conditions.

The present invention relates to a polypeptide having specific affinity for a protein partially including a CH1-CL domain forming a non-native three-dimensional structure among proteins including a CH1-CL domains of an antibody such as IgG or a Fab region thereof and a method for detecting, immobilizing, or removing the protein partially including a CH1-CL domain forming a non-native three-dimensional structure using such an affinity polypeptide.

In the present specification, the term "CH1-CL domain" means a protein associate including a CH1 domain contained in the heavy chain constant region of IgG and a CL domain contained in the light chain constant region of IgG. Here, the CH1 domain means a polypeptide portion of about 100-residue length from the N-terminus of the IgG heavy chain constant region and capable of forming a three-dimensional structure consisting of a unique domain as an immunoglobulin fold. The CL domain means a polypeptide portion of the IgG light chain constant region and capable of forming a three-dimensional structure consisting of a unique domain as an immunoglobulin fold. The CH1-CL domain may exist alone or may be a part of a protein, such as IgG or a Fab region, as long as the polypeptide of the present invention shows affinity thereto. The amino acid sequence of a constant region is known to show homology within species or also between species. For example, human IgG is classified into four subclasses of IgG1, IgG2, IgG3, and IgG4 based on the difference in the amino acid sequence of the heavy chain. In the amino acid sequences thereof, human IgG1 CH1 domain (UniProt database, Accession No. P01857), human IgG2 CH1 domain (UniProt database, Accession No. P01859), human IgG3 CH1 domain (UniProt database, Accession No. P01860), and human IgG4 CH1 domain (UniProt database, Accession No. P01861) have a sequence homology of about 90%. The amino acid sequence of the CH1 domain of human IgG1 has a sequence homology of about 65% with mouse IgG1 CH1 domain (UniProt database, Accession No. P01868) or rat IgG1 CH1 domain (UniProt database, Accession No. P20759). Example 1 described below shows the results when a CH1-CL domain derived from human IgG1 was used, but the CH1-CL domain is not limited to this, as long as the polypeptide of the present invention shows affinity to the domain. In addition, the amino acid residue of the above-mentioned CH1-CL domain may be modified (substitution, deletion, addition, and/or insertion) as long as the polypeptide of the present invention shows affinity thereto. That is, the term "CH1-CL domain" can include both the natural CH1-CL domain and a modified CH1-CL domain as long as the polypeptide of the present invention shows affinity thereto.

Formation of the non-native three-dimensional structure of a CH1-CL domain is accompanied by, for example, a change in the three-dimensional structure, and/or modification of the side chain, and/or formation of a multimer, and/or cleavage of the disulfide bond, as shown in the reference documents described below. Even when a change in the three-dimensional structure of a CH1-CL domain causes dissociation of the associate, as long as the polypeptide of the present invention shows affinity thereto, the dissociation product is also encompassed in the non-native three-dimensional structure.

In the present specification, the "non-native three-dimensional structure" is a collective term for a group of three-dimensional structures that are different from the native three-dimensional structures and arise by physical treatment, such as heating, acid treatment, stirring, shearing, protein-denaturant treatment, ionic strength change, or light irradiation; or chemical treatment with, for example, a reducing agent, an oxidant, an acid, a base, an enzyme, or a catalyst.

Here, acid treatment means, but not limited to, exposure to the condition of preferably pH 4.0 or less and more preferably pH 3.0 or less. For example, it is reported that IgG and the domain constituting IgG form a non-native three-dimensional structure, called alternatively folded state (AFS), different from the usual native three-dimensional structure by treatment with an acid buffer solution of pH 2.0 (Non Patent Literatures 14, 15, and 18).

In addition, it is known that the three-dimensional structure of a protein is generally modified by physical or chemical stress by physical or chemical treatment other than acid treatment. It is known that a three-dimensional structure is readily modified most typically by heating or a modifier such as guanidine hydrochloride (Non Patent Literature 19). For example, in the Fc region of IgG, formation of an AFS by heat modification at around 75° C. has been reported (Non Patent Literature 20). As another chemical or physical treatment, reducing agent treatment and physical shock such as shearing and stirring are widely known. The reducing agent treatment here indicates a state in which a part or whole of intramolecular or intermolecular disulfide bonds are cleaved. More specifically, the treatment indicates a state in which disulfide bonds are cleaved by addition of a reducing agent (e.g., dithiothreitol, β-mercaptoethanol, or 2-mercatoethylamine). As the physical shock such as stirring and shearing, it has been reported, but not limited to, that oxidation of amino acid residues, modification of the three-dimensional structure of a protein, and protein aggregation resulting therefrom are caused by rotating, for example, an IgG solution with a stirrer at a speed of 700 rpm (Non Patent Literatures 21 and 22). In the paragraphs 3) to 5) of Example 1 described below, the results of evaluation of affinity for IgG and a Fab region treated with an acid buffer solution are shown, but non-native three-dimensional structures occurring by treatments other than the acid treatment to which the polypeptide of the present invention shows affinity are included among the non-native three-dimensional structures of the CH1-CL domain.

One of suitable forms of the amino acid sequence of the polypeptide of the present invention is a polypeptide represented by SEQ ID NO: 1 including P-Q-x-I-x-L-x-[IL]-[NT]-[YW] (wherein x represents an amino acid residue; and brackets represent any one of the amino acid residues within the brackets) as a common sequence, and more preferably a polypeptide including an amino acid sequence represented by SEQ ID NO: 2 or 3. As described in the paragraph 5) of Example 1 and the paragraph 1) of Example 2 described below, the present invention encompasses polypeptides including amino acid sequences derived from the common sequence (SEQ ID NO: 1) by addition of several amino acid residues, for example, 1 to 20, preferably 1 to 10, more preferably 1 to 5 amino acid residues within a range that does not impair the affinity for a CH1-CL domain forming a non-native three-dimensional structure.

In addition, as shown in the paragraph 5) of Example 1 and the paragraph 1) of Example 2 described below, the present invention includes polypeptides including amino acid sequences derived from the common sequence (SEQ ID NO: 1) by deletion, substitution, or insertion of several amino acid residues, for example, 1 to 6, preferably 1 to 3, more preferably 1 or 2 amino acid residues within a range that does not impair the affinity for a CH1-CL domain forming a non-native three-dimensional structure. Examples of the amino acid sequence represented by Formula 1 include an amino acid sequence represented by SEQ ID NO: 2 or 3, and the present invention also includes polypeptides including amino acid sequences derived from the above-mentioned amino acid sequences by deletion, substitution, or insertion of 1 to 3, 1 or 2, amino acids as long as they have affinity for a CH1-CL domain forming a non-native three-dimensional structure.

In Formula 1, since the site represented by x is not important for the function of the polypeptide, it can be expected that a polypeptide having an amino acid sequence: P-Q-[DNEQHFYW]-I-[RKHSTY]-L-[GAVLIPSTY]-[IL]-[NT]-[YW] (wherein brackets represent any one of the amino acid residues within the brackets), which is obtained from the amino acid sequence represented by SEQ ID NO: 2 or 3 by conservative amino acid substitution of the sites, in particular, a polypeptide having an amino acid sequence: P-Q-[EW]-I-[RT]-L-[IT]-[IL]-[NT]-[YW] (wherein brackets represent any one of the amino acid residues within the brackets), also has the same function.

The number of the amino acid residues of the polypeptide sequence is not limited as long as the above-mentioned amino acid sequence is included. In addition, as shown by examples of affinity selection using a phage displaying an affinity polypeptide described in the paragraph 2) of Example 1 and the paragraph 1) of Example 2 described below, a recombinant phage displaying the polypeptide on the surface layer by transformation using a nucleic acid encoding the polypeptide also has affinity for the non-native three-dimensional structure of a CH1-CL domain. That is, the present invention encompasses polypeptides having the above-mentioned amino acid sequences, fusion proteins comprising the polypeptides, and transformants carrying nucleic acids encoding the polypeptides or the fusion proteins.

Further another preferred embodiment relates to a polypeptide represented by SEQ ID NO: 4 comprising, as a common sequence, Y-D-P-E-T-G-T-W-P-Q-x-I-x-L-x-[IL]-[NT]-[YW] (wherein x represents an amino acid residue, and brackets represent any one of the amino acid residues within the brackets). More preferably, the polypeptide includes an amino acid sequence represented by SEQ ID NO: 5 or 6. As in the polypeptides represented by SEQ ID NOs: 36 to 41 shown in the paragraph 1) of Example 2 described below, the present invention encompasses polypeptides comprising amino acid sequences having addition of several amino acid residues, for example, 1 to 20, preferably 1 to 10, more preferably 1 to 5 amino acid residues in the common sequence (SEQ ID NO: 4), within a range that does not impair the affinity for a CH1-CL domain forming a non-native three-dimensional structure. Examples of the amino acid sequence represented by Formula 2 include an amino acid sequence represented by SEQ ID NO: 5 or 6, and as in the polypeptides represented by SEQ ID NOs: 36 to 41 shown in the paragraph 5) of Example 1 and the paragraph 1) of Example 2 described below, the present invention also includes polypeptides comprising amino acid sequences having deletion, substitution, or insertion of several amino acid residues, for example, 1 to 6, preferably 1 to 3, and more preferably 1 or 2 amino acid residues in the common sequence (SEQ ID NO: 4), within a range that does not impair the affinity for a CH1-CL domain forming a non-native three-dimensional structure. The number of the amino acid residues of the polypeptide sequence is not limited as long as an amino acid sequence mentioned above is included.

In Formula 2, since the site represented by x is not important for the function of the polypeptide, it can be expected that a polypeptide having an amino acid sequence: Y-D-P-E-T-G-T-W-P-Q-[DNEQHFYW]-I-[RKHSTY]-L-[GAVLIPSTY]-[IL]-[NT]-[YW] (wherein brackets represent any one of the amino acid residues within the brackets), which is obtained from the amino acid sequence represented by any one of SEQ ID NOs: 5, 6, and 36 to 41 by conservative amino acid substitution of the site, in particular, a polypeptide having an amino acid sequence: Y-D-P-E-T-G-T-W-P-Q-[EW]-I-[RT]-L-[IT]-[IL]-[NT]-[YW] (wherein brackets represent any one of the amino acid residues within the brackets), also has the same function.

In addition, as shown in affinity selection using a phage displaying a polypeptide in the paragraph 2) of Example 1 and the paragraph 1) of Example 2 described below, a recombinant phage displaying the polypeptide on the surface layer by transformation using a nucleic acid encoding the polypeptide also has affinity for the CH1-CL domain forming a non-native three-dimensional structure. That is, the present invention encompasses polypeptides having the above-mentioned amino acid sequences, fusion proteins comprising the polypeptides, and transformants carrying nucleic acids encoding the polypeptides or the fusion proteins.

Further another preferred embodiment relates to a polypeptide comprising, as a common sequence: P-N-S-G-G-G-S-Y-D-P-E-T-G-T-W-P-Q-x-I-x-L-x-[IL]-[NT]-[YW] (wherein x represents an amino acid residue, and brackets represent any one of the amino acid residues within the brackets) which is represented by SEQ ID NO: 7. More preferably, the polypeptide comprises an amino acid sequence represented by SEQ ID NO: 8 or 9. As in the polypeptides represented by SEQ ID NOs: 10 to 12 shown in the paragraph 5) of Example 1 described below, the present invention encompasses polypeptides consisting of amino acid sequences having addition of several amino acid residues, for example, 1 to 20, preferably 1 to 10, more preferably 1 to 5 amino acid residues in the common sequence (SEQ ID NO: 7), within a range that does not impair the affinity for the CH1-CL domain forming a non-native three-dimensional structure. In addition, as in the polypeptides represented by SEQ ID NOs: 10 to 12 shown in the paragraph 5) of Example 1 described below, the present invention encompasses polypeptides comprising amino acid sequences having deletion, substitution, or insertion of several amino acid residues, for example, 1 to 6, preferably 1 to 3, more preferably 1 or 2 amino acid residues in the common sequence (SEQ ID NO: 7), within a range that does not impair the affinity for the CH1-CL domain forming a non-native three-dimensional structure. The number of the amino acid residues of the polypeptide sequence is not limited as long as the above-mentioned amino acid sequence is included.

In Formula 3, since the site represented by x is not important for the function of the polypeptide, it can be expected that a polypeptide having an amino acid sequence obtained from the amino acid sequence represented by any one of SEQ ID NOs: 8 to 12 by conservative amino acid substitution of the site, for example, P-N-S-G-G-G-G-S-Y-D-P-E-T-G-T-W-P-Q-[DNEQHFYW]-1-[RKHSTY]-L-[GAVLIPSTY]-[IL]-[NT]-[YW] (wherein brackets represent any one of the amino acid residues within the brackets), in particular, a polypeptide having an amino acid sequence: P-N-S-G-G-G-G-S-Y-D-P-E-T-G-T-W-P-Q-[EW]-1-[RT]-L-[IT]-[IL]-[NT]-[YW] (wherein brackets represent any one of the amino acid residues within the brackets), also has the same function.

In addition, as shown in affinity selection using a phage displaying a polypeptide in the paragraph 2) of Example 1 and the paragraph 1) of Example 2 described below, a recombinant phage displaying the polypeptide on the surface layer by transformation using a nucleic acid encoding the polypeptide also has affinity for the CH1-CL domain forming a non-native three-dimensional structure. That is, the present invention encompasses polypeptides having the above-mentioned amino acid sequences, fusion proteins comprising the polypeptides, and transformants carrying nucleic acids encoding the polypeptides or the fusion proteins.

The polypeptide of the present invention may be a tandem polypeptide having a second polypeptide at the amino-terminus, the carboxyl-terminus, or both termini as long as the polypeptide has affinity for a CH1-CL domain of immunoglobulin G. Examples of the second polypeptide include a polypeptide of the present invention to be linked for improving the affinity by a multivalent effect; a polypeptide having affinity for another molecule to be linked for imparting multispecificity; a tag polypeptide, such as a FLAG tag, a c-myc tag, or a histidine tag, to be linked for purification or detection of the polypeptide; a polypeptide forming a secondary structure, such as a leucine zipper or a β hairpin, to be linked for stabilizing the structure of the polypeptide; a signal peptide, such as an endoplasmic reticulum signal peptide, to be linked for promoting organellar localization or extracellular secretion; and an adhesive polypeptide including, for example, an RGD motif to be linked for adhesion to the cell surface. Functional improvement or multi-functionalization by linking a certain functional polypeptide with a polypeptide having the same or different function is already known in the art (Non Patent Literatures 10 and 33 to 35).

Alternatively, as described above, the polypeptide of the present invention may be a fusion protein having a protein bound to the amino-terminus, the carboxyl-terminus, or both termini of a polypeptide as long as the fusion protein has affinity for a CH1-CL domain of immunoglobulin G. Examples of the protein to be fused include a protein to be used for enhancing the solubility of the polypeptide, such as thioredoxin, maltose binding protein, or glutathione-S-transferase; a protein to be used for detecting color development, luminescence, or fluorescence, such as peroxidase, alkali phosphatase, or fluorescent protein; and a protein having affinity, such as antibody, *Staphylococcus aureus* protein A, or *Streptococcus* protein G. Improvement in solubility or multi-functionalization by binding a protein to a polypeptide having a certain function is already known in the art (Non Patent Literatures 36 to 38). Examples of the fusion protein of the present invention include proteins consisting of amino acid sequences represented by SEQ ID NOs: 13 to 15 and 42 to 46, which are encoded by nucleic acids represented by SEQ ID NOs: 16 to 18 and 47 to 51, respectively.

Furthermore, the polypeptide and the fusion protein of the present invention may be labeled. That is, the present invention encompasses a modified polypeptide, a modified protein, and a modified transformant, which are obtained by binding an organic compound, an inorganic compound, or both compounds to the above-mentioned polypeptide, fusion protein, or transformant comprising a nucleic acid encoding the polypeptide or the fusion protein, within a range that does not impair the affinity for a CH1-CL domain forming a non-native three-dimensional structure. The binding of the above-mentioned organic compound, etc. allows effective detection of a protein partially including a CH1-CL domain forming a non-native three-dimensional structure, the detection being an example of the use of the present invention shown below. Preferred examples of the organic compound, etc. include fluorescent organic compounds, such as biotin and fluorescein; fluorescent inorganic compounds, such as a stable isotope, a phosphate group, an acyl group, an amide group, an ester group, an epoxy group, polyethylene glycol (PEG), lipid, a carbohydrate chain, a nucleic acid, and a quantum dot; and colloidal gold (Non Patent Literature 23), but it is not intended to exclude any other technically applicable compounds.

There is no limitation in the use of the polypeptide of the present invention as long as the affinity for a protein partially including a CH1-CL domain forming a non-native three-dimensional structure is utilized. In general, IgG affinity molecules are used for detection (Patent Literature 5), immobilization (Non Patent Literature 24), separation/purification (Non Patent Literature 25), and removal (Patent Literature 6) of a protein including IgG or a domain derived from IgG. Accordingly, the use of the polypeptide of the present invention encompasses all technically applicable forms in the uses known to those skilled in the art including the uses utilizing IgG affinity molecules described above. As shown in Example 1 described below, the polypeptide of the present invention has specific affinity for a CH1-CL domain forming a non-native three-dimensional structure and therefore can be used for detection, immobilization, separation/purification, and removal of a protein partially including the CH1-CL domain. Examples described below show detection of non-native three-dimensional structures of IgG, a Fab region, and a CH1-CL domain, but it is not intended to exclude other usage forms.

In the present invention, the polypeptide may be synthesized by any method and may be used in any form. As the method for preparing an identified polypeptide, a large number of synthetic methods, such as an organic chemical synthetic method (Non Patent Literature 26) and a method of expressing the polypeptide as a fusion protein linked with an arbitrary protein by gene recombination (Non Patent Literature 27), have been reported, and a polypeptide of which the amino acid sequence has been identified can be easily prepared by application of an existing synthesis technique. Examples described below show preparation by organic chemical synthesis, preparation by cell expression as a fusion protein, and a recombinant phage displaying the polypeptide on the surface layer by transformation using a nucleic acid encoding the polypeptide as examples, but it is not intended to exclude other methods and the above-mentioned other techniques.

The present invention also relates to a solid-phase carrier immobilizing the polypeptide of the present invention. Here, preferred examples of the solid-phase carrier include, but not limited to, resins, such as polystyrene and polyester; biopolymer compounds, such as dextran and agarose; and inorganic materials, such as metal and glass. The solid-phase carrier may have any shape, such as a particle, a plate, a membrane, a chip, and a test tube. The polypeptide can be immobilized on such a solid-phase carrier by covalent bonding, physical adsorption, ionic bonding, or intermolecular interaction. In Example 1 described below, the peptide is immobilized on the sensor chip of a surface plasmon resonance measuring apparatus by covalent bonding, but as described above, it is not intended to exclude other supporting carriers and immobilization methods. The polypeptide of the present invention and molecules including the polypeptide, such as a fusion protein, can be suitably used for detection, immobilization, or removal of a protein partially including a CH1-CL domain forming a non-native three-dimensional structure by being immobilized on a solid-phase carrier. In Examples described below, examples of immobilizing the polypeptide of SEQ ID NO: 8 on the sensor chip of a surface plasmon resonance measuring apparatus and thereby detecting IgG and a Fab region partially including a CH1-CL forming a non-native three-dimensional structure are described, but the shape of the solid-phase carrier and the immobilization method are not limited thereto, and, for example, particles such as magnetic particles and filter membranes can be suitably applied to the methods for detecting, immobilizing, or removing proteins known to those skilled in the art. In addition, the molecules to be detected, immobilized, or removed are not limited to IgG or a Fab region and can be a protein partially including a CH1-CL domain forming a non-native three-dimensional structure, such as a fusion protein of the CH1-CL domain linked with an arbitrary protein such as a cytokine or an enzyme.

Examples of the method for measuring the affinity of a polypeptide include enzyme-linked immunosorbent assay (ELISA), surface plasmon resonance (SPR), isothermal titration calorimeter (ITC), quartz crystal microbalance (QCM), atomic force microscope (AFM) (Non Patent Literature 28), pull-down assay (Non Patent Literature 29), electrophoresis (Non Patent Literature 30), and fluorescence polarization assay (Non Patent Literature 31). Examples described below show examples of surface plasmon resonance, but it is not intended to exclude other methods and the above-mentioned other techniques.

In the present specification, "having affinity" means that a binding signal showing a value 10 or more times the binding signal/noise ratio is obtained by using any one of the above-mentioned measuring apparatuses.

It is possible to detect and/or remove a protein partially including a CH1-CL domain forming a non-native three-dimensional structure in a sample by using the polypeptide or the fusion protein of the present invention.

A method for detecting a protein partially including a CH1-CL domain forming a non-native three-dimensional structure in a test sample can comprise the following steps of:

(1) contacting a test sample with the polypeptide, the protein, the transformant, the recombinant phage or the recombinant virus, or the immobilized polypeptide or the immobilized protein of the present invention, and (2) determining whether or not a bond is formed between the test sample and the polypeptide, the protein, the transformant, the recombinant phage or the recombinant virus, or the immobilized polypeptide or the immobilized protein.

Examples of the method to be used in the step of determining whether or not a bond is formed include ELISA, SPR, ITC, QCM, AFM, pull-down assay, electrophoresis, fluorescence polarization assay, fluorescence resonance energy transfer (FRET), column chromatography, and immunochromatography. Examples described below show examples of SPR, but it is not intended to exclude other technically applicable methods and the above-mentioned other techniques.

The method for removing a protein partially including a CH1-CL domain forming a non-native three-dimensional structure in a test sample can comprise the following steps of:

(1) contacting a test sample with the polypeptide, the protein, the transformant, the recombinant phage or the recombinant virus, or the immobilized polypeptide or the immobilized protein of the present invention to bind a protein partially including a CH1-CL domain forming a non-native three-dimensional structure to the polypeptide, the protein, the transformant, the recombinant phage or the recombinant virus, or the immobilized polypeptide or the immobilized protein, and (2) removing the protein partially including a CH1-CL domain forming a non-native three-dimensional structure bound to the polypeptide, the protein, the transformant, the recombinant phage or the recombinant virus, or the immobilized polypeptide or the immobilized protein from the sample.

Examples of the method to be used in the step of collection from the above-mentioned sample include affinity chromatography, affinity bead assay, affinity filter assay, and immunoprecipitation, but it is not intended to exclude other technically applicable methods and the above-mentioned other techniques.

The present invention will now be described in detail by Examples, but is not limited to these Examples.

Example 1

In this Example, first, it will be described how the amino acid sequence of a polypeptide having affinity for a CH1-CL domain forming a non-native three-dimensional structure was identified. Next, it will be shown examples of measuring the affinity of amino acid sequences of SEQ ID NOs: 8 and 9 comprising the amino acid sequence of SEQ ID NO: 7 as a common sequence; an amino acid sequence of SEQ ID NO: 2 comprising the amino acid sequence of SEQ ID NO: 1 as a common sequence; synthetic polypeptides derived from these amino acid sequences each by addition, deletion, substitution, or insertion of several amino acid residues within a range that does not impair the affinity for the CH1-CL domain forming a non-native three-dimensional structure (or a protein partially including the CH1-CL domain forming a non-native three-dimensional structure), or fusion polypeptides (SEQ ID NOs: 13 to 15) comprising these amino acid sequences.

1) Preparation of CH1-CL Domain of Human IgG

The amino acid sequence of an affinity polypeptide was identified by affinity selection based on phage display using T7 phage. In this paragraph, an example of preparing a human IgG1-derived CH1-CL domain used for affinity selection will be described.

An expression vector pET-CH1 in which a DNA fragment encoding the amino acid sequence (SEQ ID NO: 19) of the CH1 domain having a histidine (His)6 tag at the N-terminus was introduced into pET-22b (Novagen) digested with a restriction enzyme NdeI/EcoRI was produced. Similarly, an expression vector pET-CL in which a DNA fragment encoding the amino acid sequence (SEQ ID NO: 20) of the CL domain having a histidine (His)6 tag at the N-terminus was introduced into a pET-22b vector digested with a restriction enzyme NdeI/EcoRI was produced.

*Escherichia coli* BL21(DE3) strain (Novagen) was transformed with each of the produced expression vectors by a heat shock method, and was cultured on an LB agar medium containing ampicillin at a final concentration of 100 μg/mL at 37° C. overnight. The transformants were each subcultured in 200 mL of 2×YT medium containing ampicillin at a final concentration of 100 μg/mL, and protein expression was induced at a cell density of O.D.600=0.8 with a final concentration of 1 mM isopropyl-β-D-galactopyranoside, further followed by shaking culture for 12 hours. The cells were collected by centrifugation at 7000 rpm for 20 minutes, and the resulting cell pellet was suspended in a TBS buffer solution (50 mM Tris-HCl, 150 mM NaCl, pH 7.4). The cells were ultrasonicated with Astrason 3000 (Misonix), and intracellular insoluble fraction was collected by centrifugation at 12000 rpm for 30 minutes. The collected fraction was solubilized with a protein denaturant (6 M guanidine hydrochloride, 20 mM sodium phosphate, 500 mM NaCl, pH 7.4). The target protein was purified with His GraviTrap (GE Healthcare). The resulting CH1 domain and CL domain were mixed each at a final concentration of 25 μM, and disulfide bonds were cleaved with a final concentration of 2.5 mM 2-mercaptoethanol. The resultant product was dialyzed against a refolding buffer solution (20 mM Tris-HCl, 150 mM NaCl, 1 mM EDTA, pH 8.0) at 37° C. for 6 hours to refold the denatured protein. After the dialysis, a heterodimer CH1-CL domain consisting of a CH1 domain and a CL domain was collected by gel filtration chromatography using Superdex 75 10/300 (GE Healthcare). The degree of purification of the CH1-CL domain was verified by sodium dodecyl sulfate (SDS) polyacrylamide gel electrophoresis under nonreducing conditions (FIG. 1).

2) Selection of Polypeptide Having Affinity for CH1-CL Domain Forming Non-Native Three-Dimensional Structure by Phage Display In this paragraph, an example of construction of a phage display library and affinity selection of a CH1-CL domain forming a non-native three-dimensional structure using the library will be described.

The phage display library used was that displaying artificial protein libraries (SEQ ID NOs: 21 to 24) each consisting of an amino acid sequence including microprotein chignolin and a random amino acid sequence, described in Patent Literature 3 and Non Patent Literature 12, as fusion proteins with coat protein g10 of bacteriophage T7. A specific procedure is shown below. The random amino acid residues were encoded as nucleotide sequence NNK (N represents A, G, C, or T; and K represents G or T). DNA fragments in which restriction enzyme EcoRI/HindIII digestion sites were added to each of the DNA fragments (SEQ ID NOs: 25 to 28) encoding the amino acid sequences of the artificial protein library were synthesized by polymerase chain reaction (PCR) and were digested with EcoRI and HindIII, followed by introduction into T7Select (registered trademark) 10-3 vector (Novagen). In vitro packaging of the phage was carried out using the introduced vector. Packaging was performed using T7Select (registered trademark) Packaging Kit (Novagen) in accordance with the attached instruction. The phage after packaging was infected to *Escherichia coli* BLT5403 strain (Novagen) cultured up to a cell density of O.D.600=1.0 in 200 mL of an LB medium, followed by shaking culture for 6 hours to amplify the phage. The medium supernatant was collected by centrifugation at 7000 rpm for 20 minutes, and added thereto were ⅙ volume of 50% polyethylene glycol 8000 and ⅒ volume of 5 M NaCl relative to the volume of the solution. The mixture was stirred overnight at 4° C. to precipitate the phage. The precipitate was collected by centrifugation at 12000 rpm for 20 minutes and was solubilized in a TBS-T buffer solution (20 mM Tris-HCl, 150 mM NaCl, 0.05% Tween 20 (registered trademark), pH 7.4). Aggregate in the solubilized solution was removed with a Syringe Driven filter unit (Millex) of 0.45 μm diameter to obtain a phage display library solution.

Subsequently, an example of preparation of magnetic beads immobilized with a CH1-CL domain forming a non-native three-dimensional structure to be used in affinity selection will be described. The CH1-CL domain prepared in the paragraph 1) was dialyzed against an acid buffer solution (50 mM $NaH_2PO_4$, 100 mM NaCl, pH 1.0) for 12 hours to accelerate formation of a non-native three-dimensional structure due to acid denaturation and was then dialyzed against a neutral buffer solution (50 mM $NaH_2PO_4$, 100 mM NaCl, pH 7.4) for neutralization. Subsequently, 100 μL (30 mg beads/mL) of Dynabeads M-270 Carboxylic Acid (Invitrogen) as magnetic beads was washed with 25 mM MES of pH 5.0 and was mixed with 50 μL of 50 mg/mL carbodiimide hydrochloride and 50 μL of 50 mg/mL N-hydroxysuccinimide on ice, followed by stirring at room temperature for 30 minutes. Subsequently, 60 μg of the CH1-CL domain forming a non-native three-dimensional structure was added thereto, further followed by stirring for 30 minutes. After washing with 50 mM Tris-HCl (pH 7.4), the beads were stored at 4° C.

Subsequently, an example of selecting a polypeptide having affinity for the CH1-CL domain forming a non-native three-dimensional structure using the prepared phage display library and the magnetic beads immobilized with the CH1-CL domain will be described. The magnetic beads immobilized with the CH1-CL domain forming a non-native three-dimensional structure were washed with a TBS-T buffer solution twice, and the surfaces of the magnetic beads were then blocked by contact with a blocking agent SuperBlock (registered trademark) T20 (TBS) Blocking Buffer (Thermo Fisher Scientific Inc.) for 1 hour. Subsequently, the phage display library solution was added to and mixed with the magnetic beads immobilized with the CH1-CL domain forming a non-native three-dimensional structure for 1 hour to bind the phage displaying the affinity polypeptide to the magnetic beads immobilized with the CH1-CL domain forming a non-native three-dimensional structure. Subsequently, a complex of the affinity polypeptide display phage and the magnetic beads immobilized with the CH1-CL domain forming a non-native three-dimensional structure was collected by magnetic separation. One milliliter of SuperBlock (registered trademark) T20 (TBS) Blocking Buffer (Thermo Fisher Scientific Inc.) was added to the collected complex, followed by mixing for 10 minutes. The supernatant was removed again by magnetic separation, and the beads were washed. This washing operation was repeated 10 times, and 1 mL of a TBS-T buffer solution containing 1% (w/v) sodium dodecyl sulfate (SDS) was added to the complex collected by magnetic separation, followed by mixing for 10 minutes to elute the phage displaying the affinity polypeptide from the CH1-CL domain-immobilized magnetic beads. The eluted phage was infected to *Escherichia coli* BLT5403 strain (Novagen) cultured up to a cell density of O.D.600=1.0 in 200 mL of an LB medium, followed by shaking culture for 4 hours. The medium supernatant was collected by centrifugation at 7000 rpm for 20 minutes, and added thereto were ⅙ volume of 50% polyethylene glycol 8000 and 1/10 volume of 5 M NaCl relative to the volume of the solution. The mixture was stirred overnight at 4° C. to precipitate the phage. The precipitate was collected by centrifugation at 12000 rpm for 20 minutes and was solubilized in a TBS-T buffer solution (20 mM Tris-HCl, 150 mM NaCl, 0.05% Tween 20 (registered trademark), pH 7.4). Aggregate in the solubilized solution was removed with a Syringe Driven filter unit (Millex) of 0.45 μm diameter to prepare a phage solution. The selection step described above was repeated five times to concentrate the phage displaying a polypeptide having affinity for the CH1-CL domain forming a non-native three-dimensional structure.

3) Identification of Polypeptide Having Affinity for CH1-CL Domain Forming Non-Native Three-Dimensional Structure In this paragraph, an example of determining the amino acid sequence of a polypeptide having affinity for the CH1-CL domain forming a non-native three-dimensional structure will be described.

Using as a template the solution of phage displaying the polypeptide having affinity for the CH1-CL domain forming a non-native three-dimensional structure and concentrated by affinity selection described in the preceding paragraph, the DNA of the artificial protein library region introduced into a T7 phage genome was amplified by PCR. The PCR was performed using a KOD DNA polymerase (TOYOBO CO., LTD.) under reaction conditions in accordance with the attached manual. The amplified DNA was digested with EcoRI and HindIII and introduced into the region digested at the EcoRI/HindIII site of pET-48b (Invitrogen) to construct an expression vector expressing the polypeptide, which is a translation product of the artificial protein library gene, as a fusion protein linked to the C-terminus of thioredoxin. Escherichia coli BL21 (DE3) strain was transformed by a heat shock method using the constructed expression vector and was cultured on an LB agar medium containing 50 μg/mL of kanamycin. From the resulting colonies, 36 clones were randomly isolated and were cultured with shaking in 700 μL of an LB medium. At the stage of a cell density of O.D.600=1.0, expression was induced with a final concentration of 1 mM isopropyl-β-thiogalactopyranoside, followed by culturing at 37° C. for 12 hours. The cells were collected by centrifugation at 7000 rpm, suspended in a TBS-T buffer solution, and then ultrasonicated for 20 minutes with a hermetically sealed ultrasonicator Bioruptor (COSMO BIO). The cell-disrupted solution was centrifugated at 12000 rpm, and the supernatant was collected and then roughly purified by metal chelate affinity chromatography using His SpinTrap (GE Healthcare) to prepare a thioredoxin fusion protein including the affinity polypeptide.

Figures 1, 2:
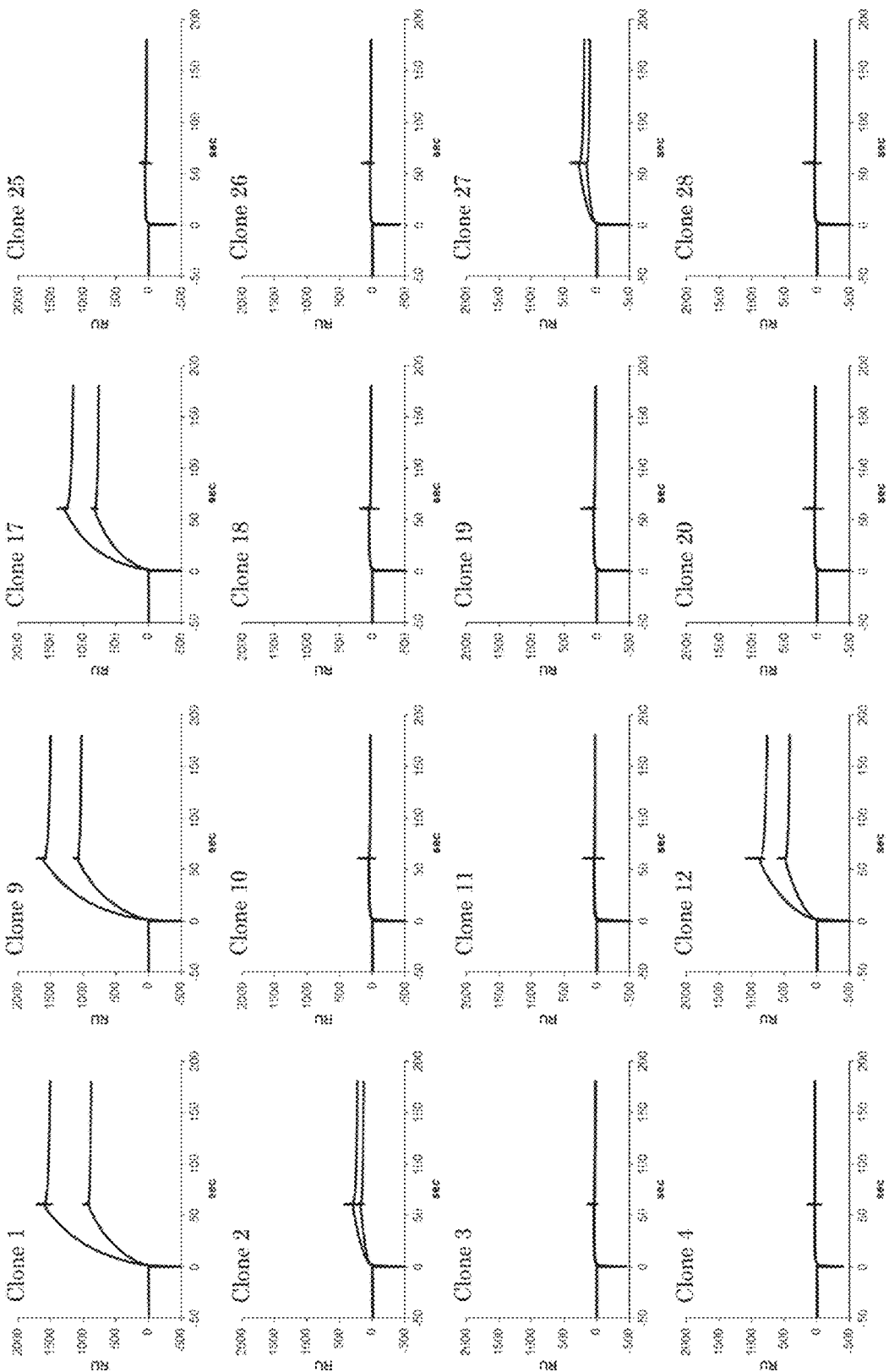
Figure 2:
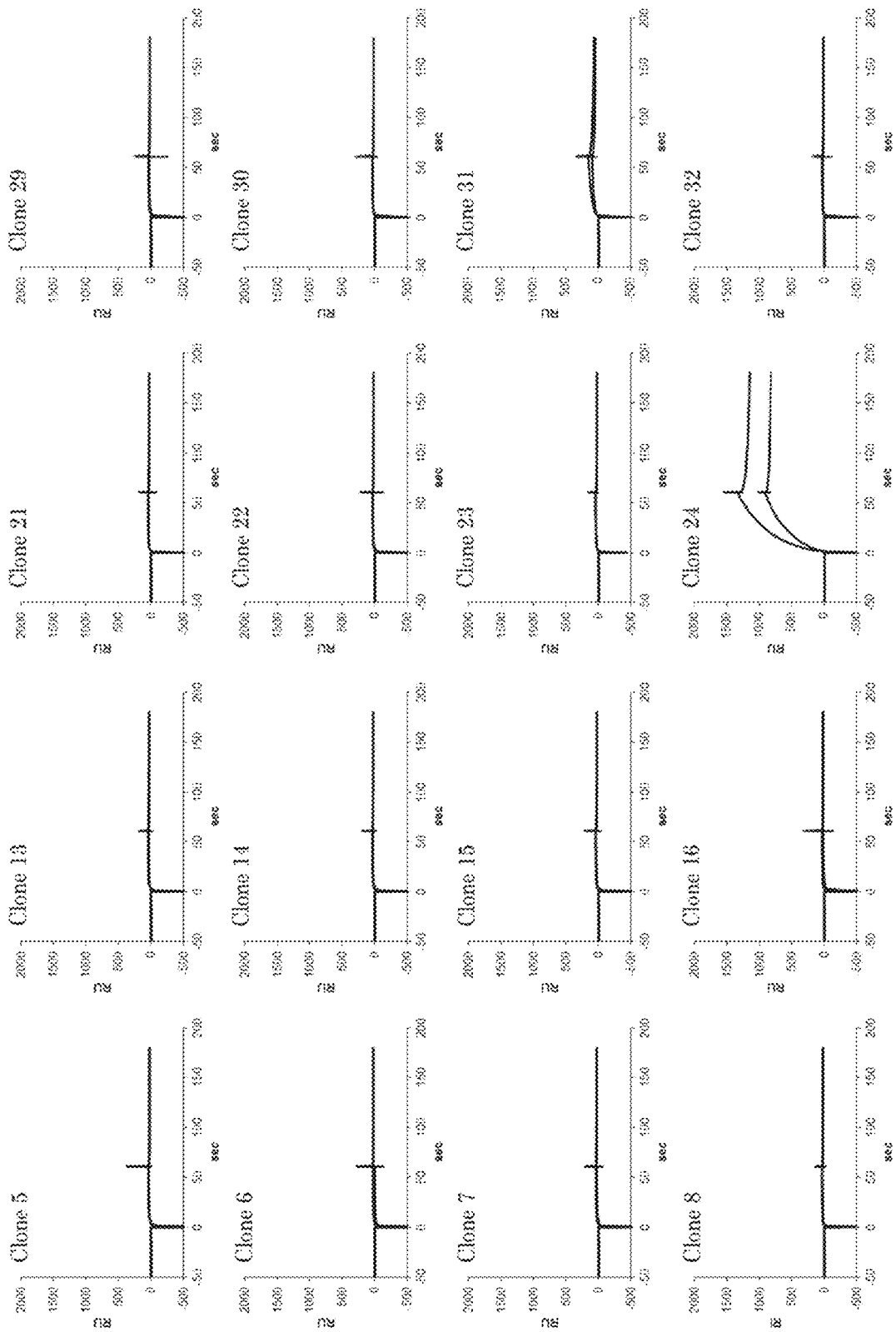

Subsequently, an example of measuring the affinity between the isolated/purified thioredoxin fusion protein and the CH1-CL domain forming a non-native three-dimensional structure by surface plasmon resonance (SPR) will be described. As the SPR measuring apparatus, Biacore T100 (GE Healthcare) was used. A CH1-CL domain was dialyzed against an acid buffer solution (50 mM NaH$_2$PO$_4$, 100 mM NaCl, pH 2.0) for 12 hours to accelerate formation of a non-native three-dimensional structure due to acid denaturation and was then dialyzed against an HBS-T buffer solution (10 mM HEPES, 150 mM NaCl, 0.05% Tween 20 (registered trademark), pH 7.4) for neutralization. The CH1-CL domain was immobilized on a sensor chip CM5 (GE Healthcare) by amine coupling. Thirty-two purified thioredoxin fusion proteins were diluted with an HBS-T buffer solution to 5 μM and 2 μM. SPR measurement was performed using an HBS-T buffer solution as the running buffer solution and 100 mM glycine-HCl of pH 2.0 as the regenerating solution at a reaction temperature of 25° C. The results of SPR sensorgrams of the 32 clones in total are shown in FIG. 2. Table 1 shows whether affinity was present or not between each of the 32 clones and the CH1-CL domain forming a non-native three-dimensional structure. Eight clones (Clone 1, Clone 2, Clone 9, Clone 12, Clone 17, Clone 24, Clone 27, and Clone 31) showed affinity for the CH1-CL domain forming a non-native three-dimensional structure (Table 1).

TABLE 1

| Clone (SEQ ID NO) | Non-native CH1-CL |
| --- | --- |
| Clone 1 (14) | Binding |
| Clone 2 (13) | Binding |
| Clone 3 (N/D) | No-binding |
| Clone 4 (N/D) | No-binding |
| Clone 5 (N/D) | No-binding |
| Clone 6 (N/D) | No-binding |
| Close 7 (N/D) | No-binding |
| Clone 8 (N/D) | No-binding |
| Clone 9 (14) | Binding |
| Clone 10 (N/D) | No-binding |
| Clone 11 (N/D) | No-binding |
| Clone 12 (14) | Binding |
| Clone 13 (N/D) | No-binding |
| Clone 14 (N/D) | No-binding |
| Clone 15 (N/D) | No-binding |
| Clone 16 (N/D) | No-binding |
| Clone 17 (14) | Binding |
| Clone 18 (N/D) | No-binding |
| Clone 19 (N/D) | No-binding |
| Clone 20 (N/D) | No-binding |
| Clone 21 (N/D) | No-binding |
| Clone 22 (N/D) | No-binding |
| Clone 23 (N/D) | No-binding |
| Clone 24 (14) | Binding |
| Clone 25 (N/D) | No-binding |
| Clone 26 (N/D) | No-binding |
| Clone 27 (14) | Binding |
| Clone 28 (N/D) | No-binding |
| Clone 29 (N/D) | No-binding |
| Clone 30 (N/D) | No-binding |
| Clone 31 (15) | Binding |
| Clone 32 (N/D) | No-binding |

Subsequently, the eight clones (Clone 1, Clone 2, Clone 9, Clone 12, Clone 17, Clone 24, Clone 27, and Clone 31) showed affinity for the CH1-CL domain forming a non-native three-dimensional structure in the SPR test were analyzed for the DNA sequences of the thioredoxin fusion proteins including the affinity polypeptides by a dideoxy method with Applied Biosystems (registered trademark) 3500 Genetic Analyzer to determine the amino acid sequences. The amino acid sequences of six clones in the eight clones were identical, and three amino acid sequences (SEQ ID NOs: 13 to 15) were finally identified as independent amino acid sequences. Regarding each of the amino acid sequences of these thioredoxin fusion proteins, the region excluding the amino acid sequences of common sequences: thioredoxin (SEQ ID NO: 29), the linker region (SEQ ID NO: 30), and microprotein chignolin (SEQ ID NO: 31) was identified as the amino acid sequence (SEQ ID NOs: 2, 3, or 32) of the region selected from random amino acid sequences by affinity selection. The amino acid sequences of the three clones have high homology and were recognized to commonly include a proline residue, a glutamine residue, an isoleucine residue, or a leucine residue.

4) Characteristic Analysis of Polypeptide Having Affinity for CH1-CL Domain Forming Non-Native Three-Dimensional Structure In this paragraph, an example of characterizing the specificity of a polypeptide having affinity for a CH1-CL domain forming a non-native three-dimensional structure will be described.

Polypeptide AF.ab9 (SEQ ID NO: 8) in which 8-residue linker sequence (Pro-Asn-Ser-Gly-Gly-Gly-Gly-Ser) (SEQ ID NO: 30) and 8-residue chignolin sequence (Tyr-Asp-Pro-Glu-Thr-Gly-Thr-Trp) (SEQ ID NO: 31) were added to the amino acid sequence (SEQ ID NO: 2) identified in the preceding paragraph was designed and organic-chemically synthesized. Preparation of the synthesized polypeptide was entrusted to GL Biochem (Shanghai). AF.ab9 was dissolved in a boric acid buffer solution (10 mM Borate-Na, 1 M NaCl, pH 8.5) and was immobilized on a sensor chip CM5 (GE Healthcare) by amine coupling.

Subsequently, human monoclonal IgG, Fab region, and Fc region having a native three-dimensional structure and a non-native three-dimensional structure were prepared. The Fab region and Fc region were prepared by subjecting human monoclonal IgG to papain digestion with Pierce (registered trademark) Fab Preparation Kit (Thermo Fisher Scientific Inc.) and then to purification by affinity chromatography using MabSelect SuRe (GE Healthcare), anion exchange chromatography using HiTrap DEAE (GE Healthcare), and gel filtration chromatography using Superdex 200 (GE Healthcare). The IgG, Fab region, and Fc region were each diluted to 5 μM and dialyzed against an acid buffer solution (50 mM NaH$_2$PO$_4$, 100 mM NaCl, pH 2.0) for 12 hours for accelerating acid denaturation and dialyzed against an HBS-T buffer solution for neutralization.

Figure 3:
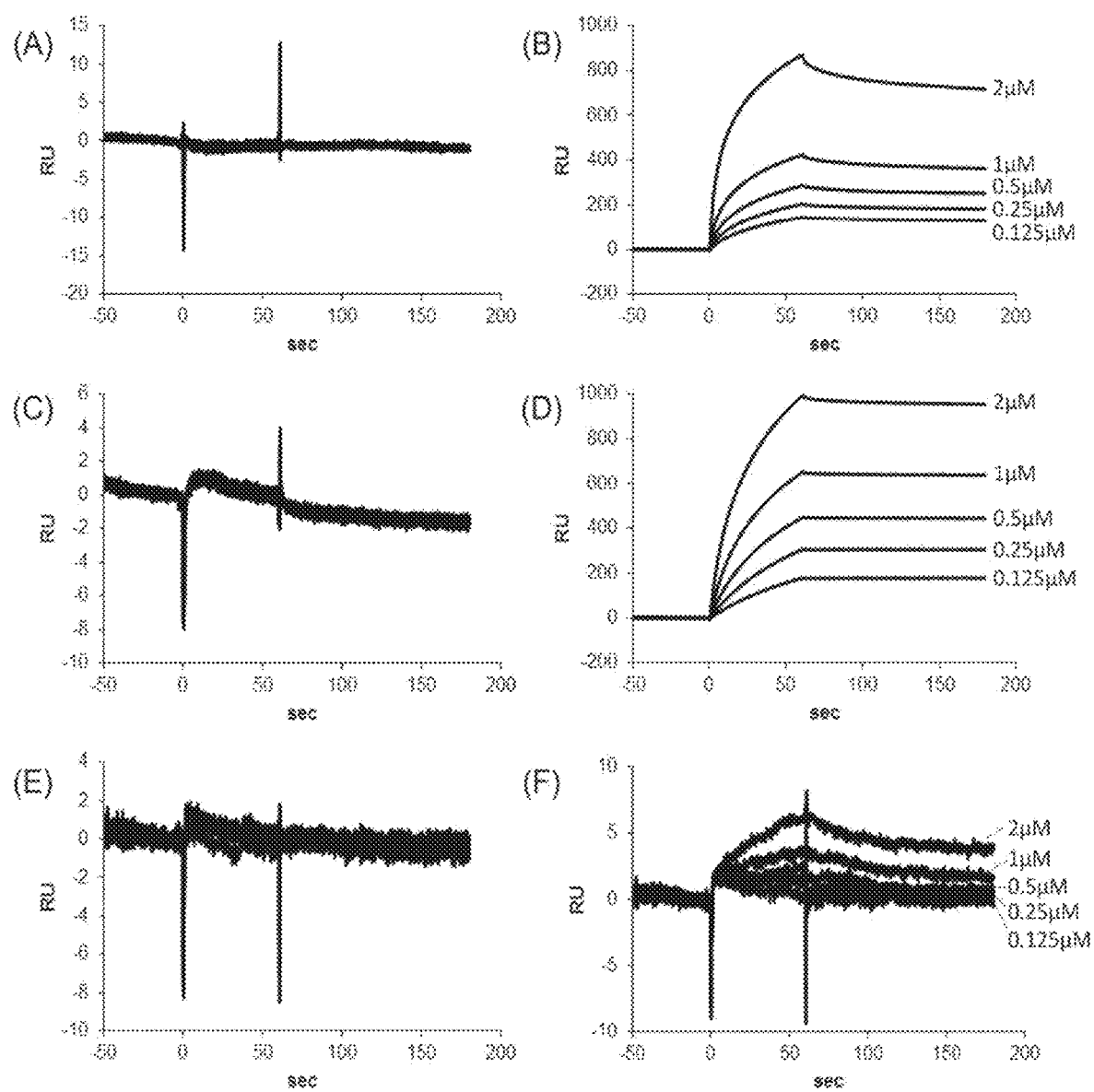
FIG. 3 shows (A) the results of evaluation, by surface plasmon resonance, of affinity between IgG (2, 1, 0.5, 0.25, and 0.125 μM) stored under neutral conditions and AF.ab9 immobilized on a sensor chip; (B) the results of evaluation, by surface plasmon resonance, of affinity between IgG (2, 1, 0.5, 0.25, and 0.125 μM) treated with an acid buffer solution of pH 2.0 and AF.ab9 immobilized on a sensor chip; (C) the results of evaluation, by surface plasmon resonance, of affinity between Fab region (2, 1, 0.5, 0.25, and 0.125 μM) stored under neutral conditions and AF.ab9 immobilized on a sensor chip; (D) the results of evaluation, by surface plasmon resonance, of affinity between Fab region (2, 1, 0.5, 0.25, and 0.125 μM) treated with an acid buffer solution of pH 2.0 and AF.ab9 immobilized on a sensor chip; (E) the results of evaluation, by surface plasmon resonance, of affinity between Fc region (2, 1, 0.5, 0.25, and 0.125 μM) stored under neutral conditions and AF.ab9 immobilized on a sensor chip; and (F) the results of evaluation, by surface plasmon resonance, of affinity between Fc region (2, 1, 0.5, 0.25, and 0.125 μM) treated with an acid buffer solution of pH 2.0 and AF.ab9 immobilized on a sensor chip. The vertical axis of each graph represents the magnitude (resonance unit) of the detection value, which reflects the weight of the molecules bonded to the sensor chip. The magnitude of the detection value depends on a plurality of measurement parameters such as the concentration and the flow rate of the specimen, but the magnitudes of the detection values when measured under the same conditions roughly correspond to the degrees of affinity of the specimens. The unit is the same between the graphs, and the same value means the same magnitude.

Acid-treated or acid-untreated IgG, Fab region, and Fc region were each diluted to 2, 1, 0.5, 0.25, and 0.125 μM and were measured for affinity for AF.ab9 with Biacore T100 (GE Healthcare) (FIG. 3, Table 2). Table 2 shows whether affinity was present or not between acid-treated IgG, acid-treated antibody domain, native IgG, or native antibody domain and AF.ab9.

TABLE 2

| IgG or antibody fragment | AF.ab9 (SEQ ID NO: 8) |
| --- | --- |
| Native IgG | No-binding |
| pH 2.0-treated IgG | Binding |
| Native Fab | No-binding |
| pH 2.0-treated Fab | Binding |
| Native Fc | No-binding |
| pH 2.0-treated Fc | No-binding |
| pH 4.0-treated IgG | No-binding |
| pH 3.0-treated IgG | Binding |

Regarding the IgG and Fab region including a CH1-CL domain, AF.ab9 did not show a significant binding response to the acid-untreated IgG and Fab region having the native three-dimensional structure (FIGS. 3 (A) and (C)), but showed a strong binding response to the acid-treated IgG and Fab region, i.e., IgG and Fab region having the CH1-CL domain forming the non-native three-dimensional structure (FIGS. 3 (B) and (D)). This result demonstrates that AF.ab9 distinguishes between the native three-dimensional structure and the non-native three-dimensional structure of IgG and Fab regions and has affinity for IgG forming a non-native three-dimensional structure and a Fab region forming a non-native three-dimensional structure. In contrast, regarding the Fc region not including a CH1-CL domain, AF.ab9 did not show a binding response to the acid-untreated Fc region having the native three-dimensional structure (FIG. 3 (E)), and the binding response to the acid-treated Fc region was only 1/100 or less compared with that on the non-native structure of the Fab region (FIG. 3 (F)). In a past report, it was observed that the CH3 domain in Fc region forms a non-native three-dimensional structure by acid treatment at pH 2 and subsequent neutralization treatment (Non Patent Literature 18). This indicates that the Fc region also forms a non-native three-dimensional structure by acid treatment as in the Fab region and further indicates that AF.ab9 specifically distinguishes the difference between the non-native three-dimensional structures of the Fab region and the Fc region. This is consistent with that the amino acid sequence included in AF.ab9 is the polypeptide selected by affinity for the CH1-CL domain forming a non-native three-dimensional structure.

Figure 4:
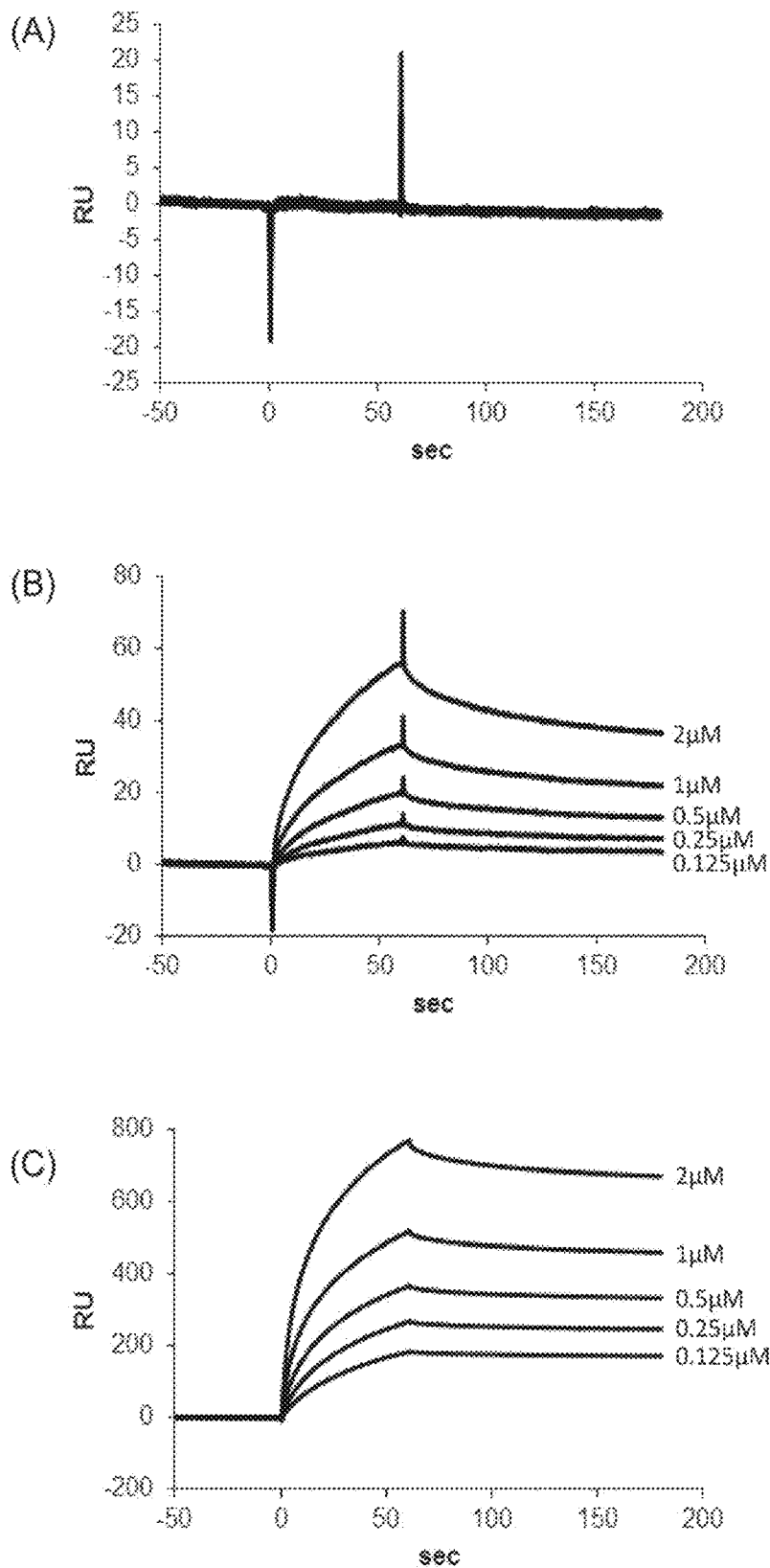
FIG. 4 shows (A) the results of evaluation, by surface plasmon resonance, of affinity between IgG (2, 1, 0.5, 0.25, and 0.125 μM) treated with an acid buffer solution of pH 4.0 and AF.ab9 immobilized on a sensor chip; (B) the results of evaluation, by surface plasmon resonance, of affinity between IgG (2, 1, 0.5, 0.25, and 0.125 μM) treated with an acid buffer solution of pH 3.0 and AF.ab9 immobilized on a sensor chip; and (C) the results of evaluation, by surface plasmon resonance, of affinity between IgG (2, 1, 0.5, 0.25, and 0.125 μM) treated with an acid buffer solution of pH 2.0 and AF.ab9 immobilized on a sensor chip. The vertical axis of each graph represents the magnitude (resonance unit) of the detection value, which reflects the weight of the molecules bonded to the sensor chip. The magnitude of the detection value depends on a plurality of measurement parameters such as the concentration and the flow rate of the specimen, but the magnitudes of the detection values when measured under the same conditions roughly correspond to the degrees of affinity of the specimens. The unit is the same between the graphs, and the same value means the same magnitude.

Subsequently, an example of evaluating the affinity of AF.ab9 for IgG treated with buffer solutions having different degrees of acidity will be described. IgG was dissolved in an HBS buffer solution (10 mM HEPES, 150 mM NaCl, pH 7.4) at a concentration of 5 μM. The acidity of a sodium phosphate buffer solution (50 mM NaH$_2$PO$_4$, 100 mM NaCl) as an acid buffer solution was adjusted to three degrees of pH 2.0, pH 3.0, and pH 4.0. An antibody was dialyzed against each of the buffer solutions for 12 hours and was then dialyzed against an HBS-T buffer solution for neutralization. The affinity of each of the resulting acid-treated IgG for AF.ab9 was measured by SPR (FIG. 4, Table 2). The SPR test was conducted in accordance with the conditions described above in this paragraph. The results of the SPR test demonstrated that AF.ab9 did not show a significant binding response to the IgG treated with the buffer solution of pH 4.0 (FIG. 4 (A)), but showed clear binding responses on the acid-treated IgG at pH 3.0 and pH 2.0 and showed a pH-dependent increase in the binding signal (FIGS. 4 (B) and (C)). This result suggests that the non-native three-dimensional structure recognized by AF.ab9 increases with the degree of acidity and that the change in the structure of the CH1-CL domain significantly occurs between pH 4.0 and pH 3.0. Regarding the acid denaturation of the CH1-CL domain, it has been reported as the results of analysis by spectroscopic methods such as CD spectrum and fluorescence spectrum that a clear change in the three-dimensional structure of the CH1-CL domain occurs between pH 4.0 and pH 3.0 (Non Patent Literature 32). The pH dependence of the binding response shown in this Example indicates that a non-native three-dimensional structure formed by acid denaturation, which has been spectroscopically proved, is detected by AF.ab9.

5) In this paragraph, an example of measuring the affinity of a polypeptide derived from a polypeptide having affinity for the CH1-CL domain forming a non-native three-dimensional structure by addition, deletion, or substitution of one or several amino acid residues in the amino acid sequence will be described.

Figure 5:
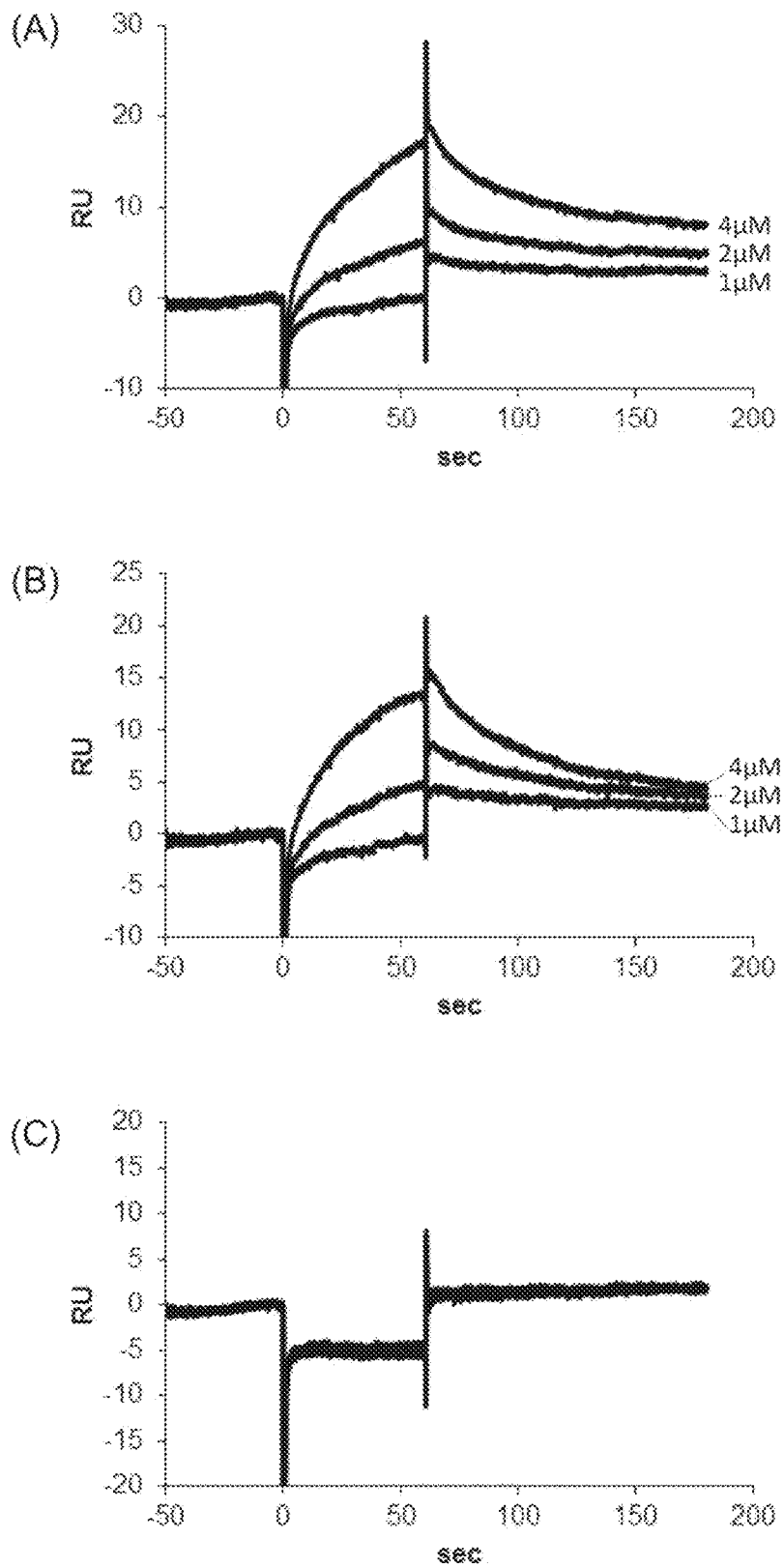
FIG. 5 shows (A) the results of evaluation, by surface plasmon resonance, of affinity between AF.ab9 (4, 2, and 1 μM) and a CH1-CL domain forming a non-native three-dimensional structure and immobilized on a sensor chip; (B) the results of evaluation, by surface plasmon resonance, of affinity between AF.ab9 arm (4, 2, and 1 μM) and a CH1-CL domain forming a non-native three-dimensional structure and immobilized on a sensor chip; and (C) the results of evaluation, by surface plasmon resonance, of affinity between AF.ab9 body (4, 2, and 1 μM) and a CH1-CL domain forming a non-native three-dimensional structure and immobilized on a sensor chip. The vertical axis of each graph represents the magnitude (resonance unit) of the detection value, which reflects the weight of the molecules bonded to the sensor chip. The magnitude of the detection value depends on a plurality of measurement parameters such as the concentration and the flow rate of the specimen, but the magnitudes of the detection values when measured under the same conditions roughly correspond to the degrees of affinity of the specimens. The unit is the same between the graphs, and the same value means the same magnitude.

AF.ab9 consists of three regions, i.e., an 8-residue linker region (SEQ ID NO: 30), a region consisting of 8-residue microprotein chignolin (SEQ ID NO: 31), and a region selected from the 10-residue random amino acid sequences by affinity selection in the paragraph 2). In order to verify the participation, in the affinity, of the region selected from the random amino acid sequences among these components, the following three polypeptides, AF.ab9 (SEQ ID NO: 8), AF.ab9 body (SEQ ID NO: 33), and AF.ab9 arm (SEQ ID NO: 2), were organic-chemically synthesized. Here, the AF.ab9 body is a 16-residue polypeptide consisting of the 8-residue linker region and the 8-residue microprotein chignolin, and the AF.ab9 arm is a 10-residue polypeptide consisting of a region selected from the random amino acid sequences. The preparation of the polypeptides was entrusted to GL Biochem (Shanghai). A peptide was diluted to 4, 2, and 1 µM with an HBS-T buffer solution, and the affinity thereof for the CH1-CL domain forming a non-native three-dimensional structure prepared by the same method as in the paragraph 3) was measured with Biacore T100 (GE Healthcare) (FIG. 5, Table 3). The measurement conditions were in accordance with those in the paragraph 3). Table 3 shows whether affinity was present or not between each synthetic peptide and the CH1-CL domain forming a non-native three-dimensional structure.

TABLE 3

| Peptide (SEQ ID NO) | Non-native CH1-CL domain |
|---|---|
| AF.ab9 (8) | Binding |
| AF.ab9 arm (2) | Binding |
| AF.ab9 body (33) | No-binding |
| AF.ab31 (9) | Binding |
| AF.ab9 P17A (10) | Binding |
| AF.ab9 Q18A (11) | Binding |
| AF.ab9 L24A (12) | Binding |

AF.ab9 and AF.ab9 arm showed affinity for the CH1-CL domain forming a non-native three-dimensional structure (FIGS. 5 (A) and (B)). In contrast, AF.ab9 body consisting of the linker region and chignolin did not show significant affinity (FIG. 5 (C)). This indicates that the region having affinity in AF.ab9 is the region selected from the 10-residue random amino acid sequences and that the affinity for the CH1-CL domain forming a non-native three-dimensional structure is maintained even when a non-affinity polypeptide, such as a linker region, is added to the affinity polypeptide.

Subsequently, an example of measuring the affinity of a polypeptide derived from an affinity polypeptide by substitution of one or several amino acid residues in the amino acid sequence and an example of evaluating the influence of the amino acid residue showing convergence in affinity selection on the affinity among the 10-residue amino acid sequences selected by affinity selection will be described.

AF.ab31 (SEQ ID NO: 9), which is one of the amino acid sequences identified by affinity selection, was selected as an example of the polypeptide derived from AF.ab9 by substitution of several amino acid residues and was organic-chemically synthesized. The preparation of the polypeptide was entrusted to GL Biochem (Shanghai).

Incidentally, as a method for identifying an amino acid residue important for a function, mutant analysis (alanine scanning) by substituting a target residue with an alanine residue is generally employed. Here, alanine scanning was performed for the amino acid residue at the site particularly showed convergence of the sequence in affinity selection, and the influence of the amino acid residue on the affinity was evaluated. Variants, AF.ab9 P17A (SEQ ID NO: 10), AF.ab9 Q18A (SEQ ID NO: 11), and AF.ab9 L24A (SEQ ID NO: 12) in which the proline residue at position 17 (Pro17), the glutamine residue at position 18 (Qln18), and the leucine residue at position 24 (Leu24) showing convergence in affinity selection were substituted with alanine residues were organic-chemically synthesized. The preparation of the polypeptide was entrusted to GL Biochem (Shanghai).

Figure 6:
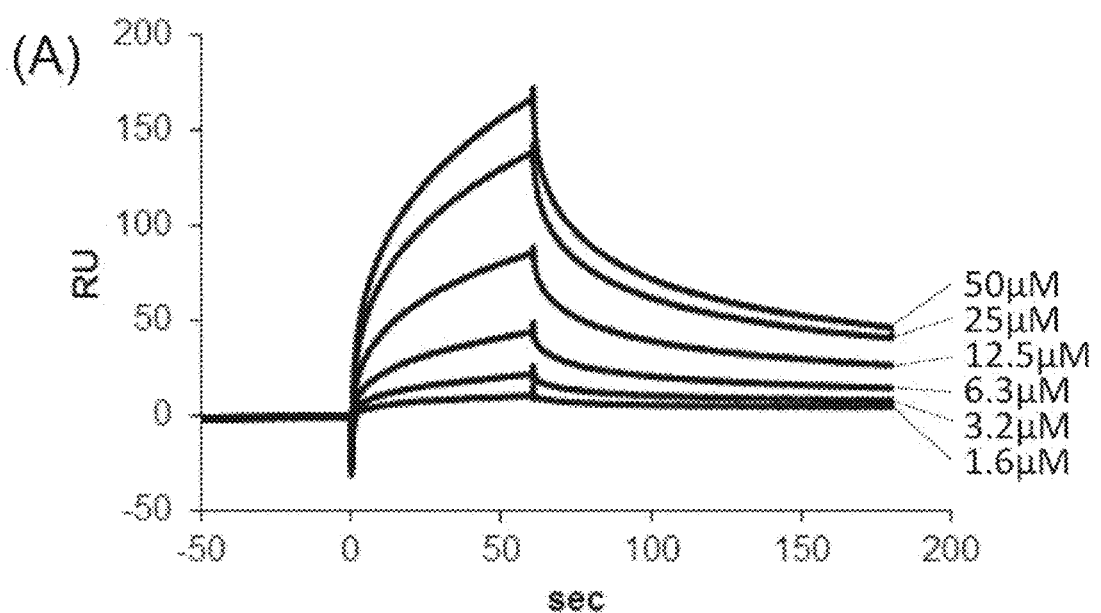
FIG. 6 shows (A) the results of evaluation, by surface plasmon resonance, of affinity between AF.ab9 (50, 25, 12.5, 6.3, 3.2, and 1.6 μM) and a CH1-CL domain forming a non-native three-dimensional structure and immobilized on a sensor chip; and (B) the results of evaluation, by surface plasmon resonance, of affinity between AF.ab31 (50, 25, 12.5, 6.3, 3.2, and 1.6 μM) and a CH1-CL domain forming a non-native three-dimensional structure and immobilized on a sensor chip. The vertical axis of each graph represents the magnitude (resonance unit) of the detection value, which reflects the weight of the molecules bonded to the sensor chip. The magnitude of the detection value depends on a plurality of measurement parameters such as the concentration and the flow rate of the specimen, but the magnitudes of the detection values when measured under the same conditions roughly correspond to the degrees of affinity of the specimens. The unit is the same between the graphs, and the same value means the same magnitude.
Figure 6:
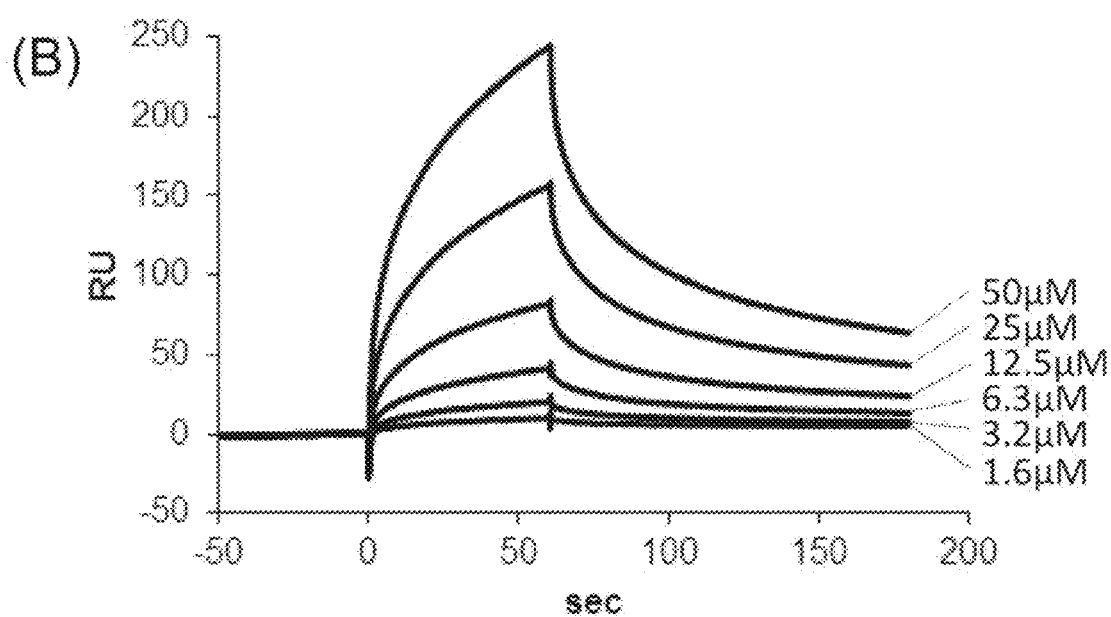
Figure 7:
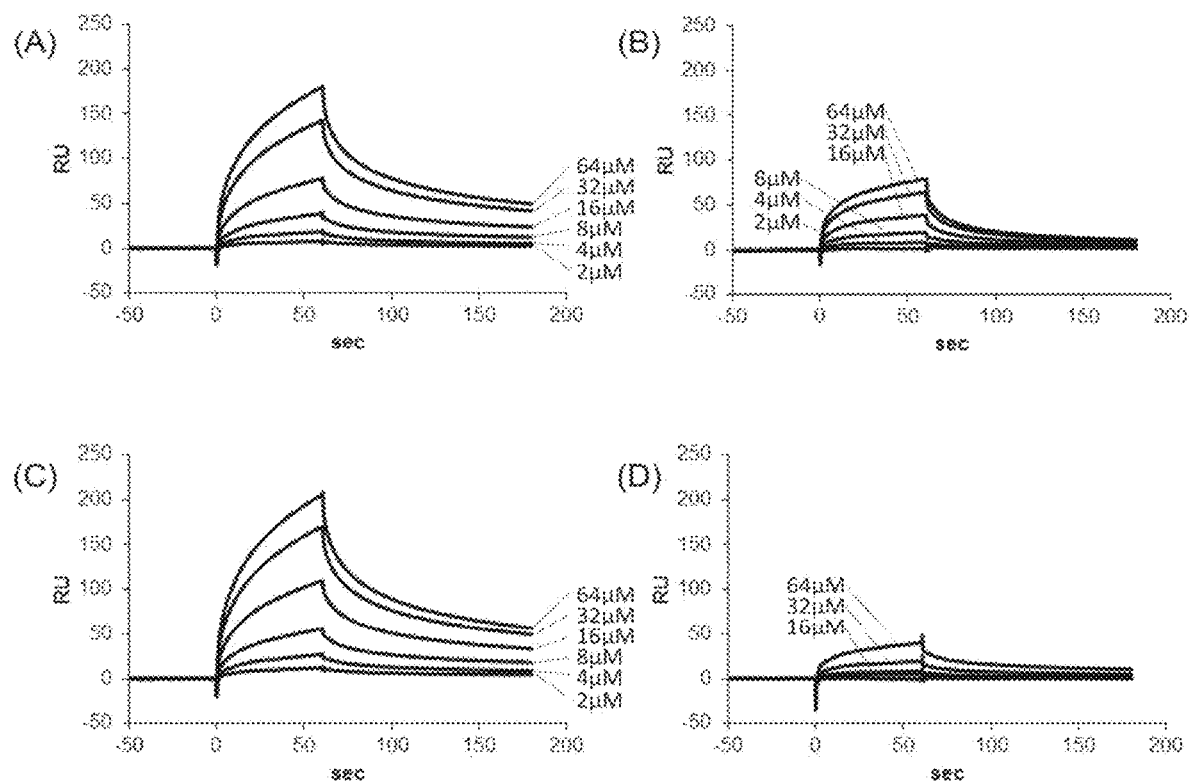
FIG. 7 shows (A) the results of evaluation, by surface plasmon resonance, of affinity between AF.ab9 (64, 32, 16, 8, 4, and 2 μM) and a CH1-CL domain forming a non-native three-dimensional structure and immobilized on a sensor chip; (B) the results of evaluation, by surface plasmon resonance, of affinity between AF.ab9 P17A (64, 32, 16, 8, 4, and 2 μM) and a CH1-CL domain forming a non-native three-dimensional structure and immobilized on a sensor chip; (C) the results of evaluation, by surface plasmon resonance, of affinity between AF.ab9 Q18A (64, 32, 16, 8, 4, and 2 μM) and a CH1-CL domain forming a non-native three-dimensional structure and immobilized on a sensor chip; and (D) the results of evaluation, by surface plasmon resonance, of affinity between AF.ab9 L24A (64, 32, 16, 8, 4, and 2 μM) and a CH1-CL domain forming a non-native three-dimensional structure and immobilized on a sensor chip. The vertical axis of each graph represents the magnitude (resonance unit) of the detection value, which reflects the weight of the molecules bonded to the sensor chip. The magnitude of the detection value depends on a plurality of measurement parameters such as the concentration and the flow rate of the specimen, but the magnitudes of the detection values when measured under the same conditions roughly correspond to the degrees of affinity of the specimens. The unit is the same between the graphs, and the same value means the same magnitude.

The CH1-CL domain forming a non-native three-dimensional structure prepared by the same method as in the paragraph 3) was immobilized on a sensor chip CM5 (GE Healthcare) by amine coupling, and the binding thereof to AF.ab31, AF.ab9, and alanine substitution products was measured with Biacore T100 (FIGS. 6 and 7, Table 3).

The affinity of AF.ab31 (FIG. 6 (B)) was substantially equivalent to the measurement result of AF.ab9 (FIG. 6 (A)). Based on this result, a common sequence involved in the affinity was examined from the amino acid sequences of AF.ab31 and AF.ab9. The results of the above-described affinity test (FIG. 5) indicate that the site involved in the affinity is a region derived from a 10-residue random amino acid sequence. Comparison of the amino acid sequences of AF.ab31 and AF.ab9 in this region demonstrated that the amino acid residues of four sites of positions 17, 18, 20, and 22 were perfectly identical; the amino acid residues of three sites of positions 24, 25, and 26 were identical as amino acid residues showing similar physical properties, such as a hydrophobic amino acid residue (leucine or isoleucine), a polar amino acid residue (asparagine or threonine), and a polar aromatic ring amino acid residue (tryptophan or tyrosine); and three sites of positions 19, 21, and 23 were substituted as the amino acid residues different in properties. Based on this result, Formulas 1, 2, and 3 (SEQ ID NOs: 1, 4, and 7) were deduced as common sequences having affinity.

In variants, AF.ab9 P17A and AF.ab9 L24A in which the proline residue at position 17 and the leucine residue at position 24, respectively, were substituted with alanine residues, the binding response decreased compared to the measurement results of AF.ab9 (FIG. 7 (A)), which suggested that these residues are important for affinity for the CH1-CL domain forming a non-native three-dimensional structure (FIGS. 7 (B) and (D)). In contrast, substitution of the glutamine residue at position 18 with an alanine residue did not largely decrease the affinity for the CH1-CL domain forming a non-native three-dimensional structure (FIG. 7 (C)).

Example 2

In this Example, amino acid sequences of SEQ ID NOs: 36 to 41 comprising the amino acid sequence of SEQ ID NO: 5 as a common sequence were identified as polypeptides having affinity for a CH1-CL domain forming a non-native three-dimensional structure, and an example measuring the affinity of fusion proteins comprising these amino acid sequences for the CH1-CL domain will be described.

1) In this paragraph, an example of constructing a phage display library and identifying the amino acid sequence of an affinity polypeptide using the library by affinity selection for a CH1-CL domain forming a non-native three-dimensional structure will be described. The phage display library used was that displaying an artificial protein library (SEQ ID NO: 34) consisting of an amino acid sequence including a 10-amino acid residue random amino acid sequence on the N-terminus side of the amino acid sequence (SEQ ID NO: 5) identified in Example 1 as a fusion protein with coat protein g10 of bacteriophage T7. A specific procedure is shown below. The random amino acid residue was encoded by a nucleotide sequence NNK (N represents A, G, C, or T; and K represents G or T). A DNA fragment in which a DNA encoding a restriction enzyme EcoRI digestion site and a (Gly)$_4$-Ser linker was added to the 5' end of the DNA fragment (SEQ ID NO: 35) encoding the amino acid sequence of the artificial protein library and a stop codon and a HindIII digestion site were added to the 3' end of the DNA fragment was synthesized by polymerase chain reaction (PCR) and was digested with EcoRI and HindIII, followed by introduction into T7Select (registered trademark) 1-1 vector (Merck KGaA). In vitro packaging of the phage was carried out using the introduced vector. Packaging was performed using T7Select (registered trademark) Packaging Kit (Merck KGaA) in accordance with the attached instruction. The phage after packaging was infected to *Escherichia coli* BLT5403 strain (Merck KGaA) cultured up to a cell density of O.D.600=1.0 in 200 mL of an LB medium, followed by shaking culture for 6 hours to amplify the phage. The medium supernatant was collected by centrifugation at 7000 rpm for 20 minutes, and added thereto were ⅙ volume of 50% polyethylene glycol 8000 and ⅒ volume of 5 M NaCl relative to the volume of the solution. The mixture was stirred overnight at 4° C. to precipitate the phage. The precipitate was collected by centrifugation at 12000 rpm for 20 minutes and was solubilized in a TBS-T buffer solution (20 mM Tris-HCl, 150 mM NaCl, 0.05% Tween 20 (registered trademark), pH 7.4). Aggregate in the solubilized solution was removed with a Syringe Driven filter unit (Millex) of 0.45 μm diameter to prepare a phage display library solution.

Subsequently, an example of selecting a polypeptide having affinity for the CH1-CL domain forming a non-native three-dimensional structure using the prepared phage display library will be described. The CH1-CL domain was prepared by the same method as in Example 1. Biotin was chemically bonded to the prepared CH1-CL domain via an amino group using Biotinamidohexanoic acid N-hydroxysuccinimide ester (SIGMA-ALDRICH Japan LLC). The CH1-CL domain was dialyzed against an acid buffer solution (50 mM $NaH_2PO_4$, 100 mM NaCl, pH 1.0) for 12 hours to accelerate formation of a non-native three-dimensional structure due to acid denaturation and was then dialyzed against a neutral buffer solution (50 mM $NaH_2PO_4$, 100 mM NaCl, pH 7.4) for neutralization. The CH1-CL domain forming a non-native three-dimensional structure was immobilized on magnetic beads Streptavidin MagneSphere (registered trademark) Paramagnetic Particles (Promega Corporation). The immobilized magnetic beads were washed with a TBS-T buffer solution twice, and the surfaces of the magnetic beads were then blocked by contact with a blocking agent SuperBlock (registered trademark) T20 (TBS) Blocking Buffer (Thermo Fisher Scientific Inc.) for 1 hour. Subsequently, the phage display library solution was added to the magnetic beads immobilized with the CH1-CL domain forming a non-native three-dimensional structure, followed by mixing for 1 hour to bind the phage displaying the affinity polypeptide to the magnetic beads immobilized with the CH1-CL domain forming a non-native three-dimensional structure. Subsequently, a complex of the affinity polypeptide display phage and the magnetic beads immobilized with the CH1-CL domain forming a non-native three-dimensional structure was collected by magnetic separation. One milliliter of SuperBlock (registered trademark) T20 (TBS) Blocking Buffer (Thermo Fisher Scientific Inc.) was added to the collected complex, mixing was performed for 10 minutes, the supernatant was removed again by magnetic separation, and the beads were washed. This washing operation was repeated 10 times, and 1 mL of a TBS-T buffer solution containing 1% (w/v) sodium dodecyl sulfate (SDS) was added to the complex collected by magnetic separation, followed by mixing for 10 minutes to elute the phage displaying the affinity polypeptide from the CH1-CL domain-immobilized magnetic beads. The eluted phage was infected to *Escherichia coli* BLT5403 strain (Merck KGaA) cultured up to a cell density of O.D.600=1.0 in 200 mL of an LB medium, followed by shaking culture for 4 hours. The medium supernatant was collected by centrifugation at 7000 rpm for 20 minutes, and added thereto were ⅙ volume of 50% polyethylene glycol 8000 and ⅒ volume of 5 M NaCl relative to the volume of the solution. The mixture was stirred overnight at 4° C. to precipitate the phage. The precipitate was collected by centrifugation at 12000 rpm for 20 minutes and was solubilized in a TBS-T buffer solution (20 mM Tris-HCl, 150 mM NaCl, 0.05% Tween 20 (registered trademark), pH 7.4). Aggregate in the solubilized solution was removed with a Syringe Driven filter unit (Millex) of 0.45 μm diameter to prepare a phage solution. The selection step described above was repeated six times to concentrate the phage displaying a polypeptide having affinity for the CH1-CL domain forming a non-native three-dimensional structure. Thirty-two clones were randomly isolated from concentrated phage group, and the amino acid sequence of the affinity polypeptide region was analyzed using Applied Biosystems (registered trademark) 3500 Genetic Analyzer. Duplication was recognized in the amino acid sequences of the affinity polypeptides of the isolated clones, and six affinity polypeptides having independent amino acid sequences were identified (SEQ ID NOs: 36 to 41).

2) In this paragraph, an example of preparing a thioredoxin fusion protein with an affinity polypeptide consisting of the amino acid sequence identified in the preceding paragraph and measuring the affinity for the CH1-CL domain forming a non-native three-dimensional structure using the thioredoxin fusion protein will be described.

The DNA region encoding the affinity polypeptide region was amplified by PCR using each of the phage solutions displaying affinity polypeptides (SEQ ID NOs: 36 to 40) consisting of the amino acid sequences identified in the preceding paragraph as templates. The PCR was performed using a KOD DNA polymerase (TOYOBO CO., LTD.) under reaction conditions in accordance with the attached manual. The amplified DNA was digested with EcoRI and HindIII and introduced into the region digested at the EcoRI/HindIII site of pET-48b (Merck KGaA) to construct an expression vector expressing the affinity polypeptide as a fusion protein linked to the C-terminus of thioredoxin. *Escherichia coli* BL21 (DE3) strain (Merck KGaA) was transformed by a heat shock method using the constructed expression vector and was cultured on an LB agar medium containing 50 μg/mL of kanamycin. The transformant was cultured with shaking in 200 mL of 2×YT medium, and at the stage of a cell density of O.D.600=1.0, expression was induced with a final concentration of 1 mM isopropyl-β-thiogalactopyranoside, followed by culturing at 37° C. for 12 hours. The cells were collected by centrifugation at 7000 rpm, suspended in a TBS-T buffer solution, and then ultrasonicated. The cell-disrupted solution was centrifuged at 12000 rpm, and the supernatant was collected and then purified by metal chelate affinity chromatography using His SpinTrap (GE Healthcare) to prepare a thioredoxin fusion proteins (SEQ ID NOs: 42 to 46) including the affinity polypeptides.

Figure 8:
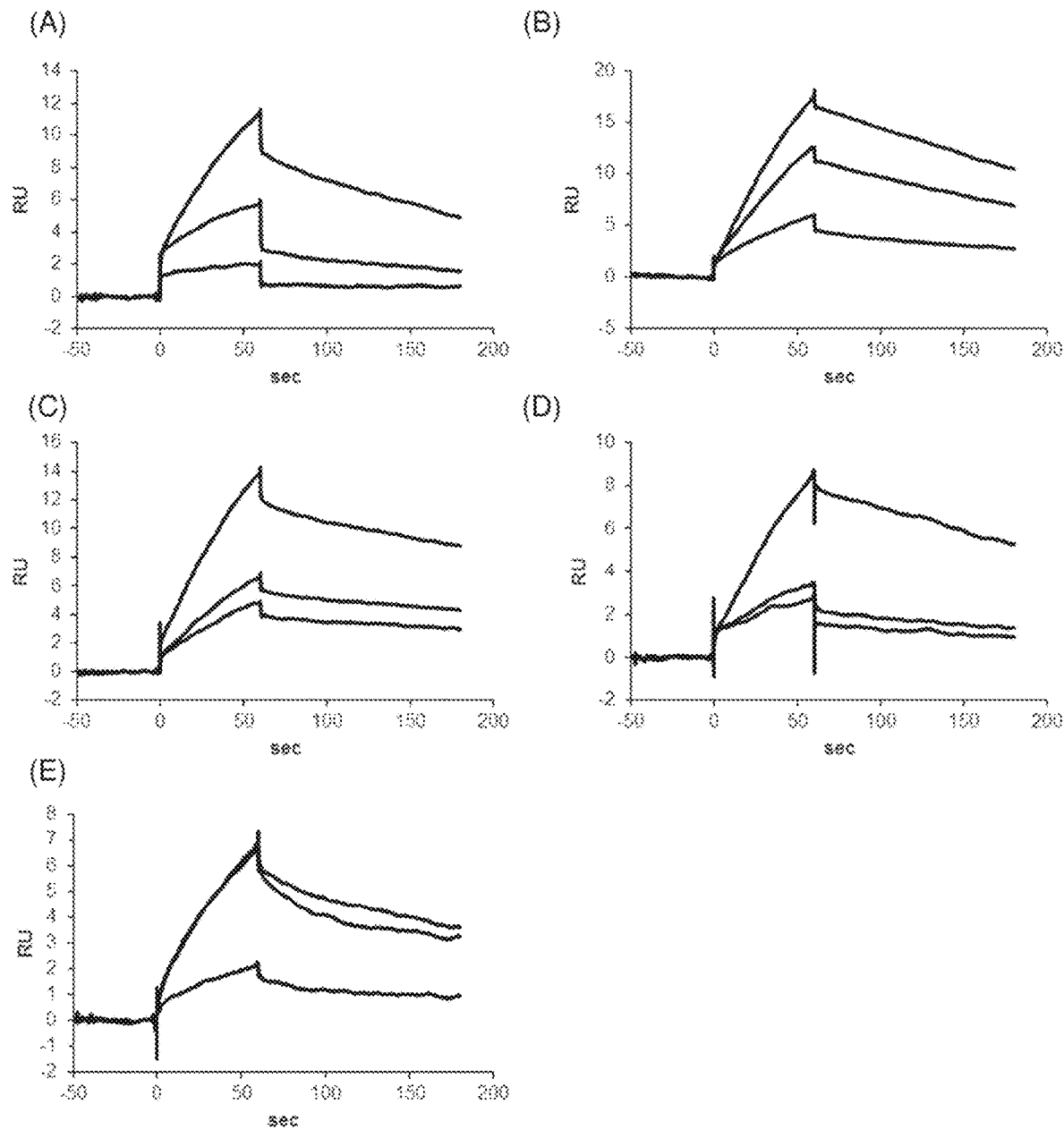
FIG. 8 shows (A) the results of evaluation, by surface plasmon resonance, of affinity between fusion protein Trx_clone1_2 (SEQ ID NO: 42) including an affinity polypeptide prepared as a thioredoxin fusion protein (10, 5, and 2.5 nM) and a CH1-CL domain forming a non-native three-dimensional structure and immobilized on a sensor chip; (B) the results of evaluation, by surface plasmon resonance, of affinity between fusion protein Trx_clone2_2 (SEQ ID NO: 43) including an affinity polypeptide prepared as a thioredoxin fusion protein (10, 5, and 2.5 nM) and a CH1-CL domain forming a non-native three-dimensional structure and immobilized on a sensor chip; (C) the results of evaluation, by surface plasmon resonance, of affinity between fusion protein Trx_clone3_2 (SEQ ID NO: 44) including an affinity polypeptide prepared as a thioredoxin fusion protein (10, 5, and 2.5 nM) and a CH1-CL domain forming a non-native three-dimensional structure and immobilized on a sensor chip; (D) the results of evaluation, by surface plasmon resonance, of affinity between fusion protein Trx_clone13_2 (SEQ ID NO: 45) including an affinity polypeptide prepared as a thioredoxin fusion protein (10, 5, and 2.5 nM) and a CH1-CL domain forming a non-native three-dimensional structure and immobilized on a sensor chip; and (E) the results of evaluation, by surface plasmon resonance, of affinity between fusion protein Trx_clone20_2 (SEQ ID NO: 46) including an affinity polypeptide prepared as a thioredoxin fusion protein (10, 5, and 2.5 nM) and a CH1-CL domain forming a non-native three-dimensional structure and immobilized on a sensor chip.

Subsequently, an example of measuring the affinity between the prepared thioredoxin fusion protein and the CH1-CL domain forming a non-native three-dimensional structure by surface plasmon resonance (SPR) will be described. As the SPR measuring apparatus, Biacore T200 (GE Healthcare) was used. The CH1-CL domain was dialyzed against an acid buffer solution (50 mM $NaH_2PO_4$, 100 mM NaCl, pH 1.0) for 12 hours to accelerate formation of a non-native three-dimensional structure due to acid denaturation and was then dialyzed against an HBS-T buffer solution (10 mM HEPES, 150 mM NaCl, 0.05% Tween 20 (registered trademark), pH 7.4) for neutralization. The CH1-CL domain was immobilized on a sensor chip CM5 (GE Healthcare) by amine coupling. SPR measurement was performed using the prepared thioredoxin fusion protein as the analyte, an HBS-T buffer solution as the running buffer solution, and 100 mM glycine-HCl of pH 2.0 as the regenerating solution at a reaction temperature of 25° C. The results of SPR sensorgrams of the thioredoxin fusion proteins (SEQ ID NOs: 42 to 46) are shown in FIG. 8 (A) to (E). The measurement data was treated with Biacore T200 Evaluation Software (GE Healthcare), and the affinity was calculated as the equilibrium dissociation constant $K_D$. The results are shown in Table 4.

TABLE 4

| Clone (SEQ ID NO) | $K_D$ (nM) |
|---|---|
| Trx_clone 1_2 (42) | 4.5 |
| Trx_clone 2_2 (43) | 3.0 |
| Trx_clone 3_2 (44) | 2.5 |
| Trx_clone 13_2 (45) | 2.8 |
| Trx_clone 20_2 (46) | 2.2 |

INDUSTRIAL APPLICABILITY

The polypeptide of the present invention has specific affinity for proteins partially including a CH1-CL domain of immunoglobulin G, the CH1-CL domain being forming a non-native three-dimensional structure, and is therefore useful for detection, immobilization, or removal of these proteins.

All publications, patents, and patent applications cited in the present specification are incorporated herein by reference in their entirety.

Sequence Listing Free Text

SEQ ID NO: 1: IgG binding peptide
SEQ ID NO: 2: IgG binding peptide
SEQ ID NO: 3: IgG binding peptide
SEQ ID NO: 4: IgG binding peptide
SEQ ID NO: 5: IgG binding peptide
SEQ ID NO: 6: IgG binding peptide
SEQ ID NO: 7: IgG binding peptide
SEQ ID NO: 8: IgG binding peptide
SEQ ID NO: 9: IgG binding peptide
SEQ ID NO: 10: IgG binding peptide
SEQ ID NO: 11: IgG binding peptide
SEQ ID NO: 12: IgG binding peptide
SEQ ID NO: 13: IgG binding peptide
SEQ ID NO: 14: IgG binding peptide
SEQ ID NO: 15: IgG binding peptide
SEQ ID NO: 16: oligo DNA
SEQ ID NO: 17: oligo DNA
SEQ ID NO: 18: oligo DNA
SEQ ID NO: 21: peptide library
SEQ ID NO: 22: peptide library
SEQ ID NO: 23: peptide library
SEQ ID NO: 24: peptide library
SEQ ID NO: 25: oligo DNA
SEQ ID NO: 26: oligo DNA
SEQ ID NO: 27: oligo DNA
SEQ ID NO: 28: oligo DNA
SEQ ID NO: 30: synthetic peptide
SEQ ID NO: 31: synthetic peptide
SEQ ID NO: 32: IgG binding peptide
SEQ ID NO: 33: synthetic peptide
SEQ ID NO: 34: peptide library
SEQ ID NO: 35: oligo DNA
SEQ ID NO: 36: IgG binding peptide
SEQ ID NO: 37: IgG binding peptide
SEQ ID NO: 38: IgG binding peptide
SEQ ID NO: 39: IgG binding peptide
SEQ ID NO: 40: IgG binding peptide
SEQ ID NO: 41: IgG binding peptide
SEQ ID NO: 42: IgG binding peptide
SEQ ID NO: 43: IgG binding peptide
SEQ ID NO: 44: IgG binding peptide
SEQ ID NO: 45: IgG binding peptide
SEQ ID NO: 46: IgG binding peptide
SEQ ID NO: 47: oligo DNA
SEQ ID NO: 48: oligo DNA
SEQ ID NO: 49: oligo DNA
SEQ ID NO: 50: oligo DNA
SEQ ID NO: 51: oligo DNA

The invention claimed is:

1. A polypeptide comprising the amino acid sequence of the following Formula 1:

(SEQ ID NO: 1)
P-Q-x-I-x-L-x-[IL]-[NT]-[YW], wherein x represents an amino acid residue, and brackets represent any one of the amino acid residues within the brackets, wherein the polypeptide has affinity for a CH1-CL domain of immunoglobulin G, and wherein the polypeptide comprises the amino acid sequence of SEQ ID NO: 2 or 3.

2. The polypeptide according to claim 1, wherein said polypeptide has 1-20 amino acid residues added to the N-terminus, the C-terminus, or both, of the amino acid sequence of Formula 1.

3. A kit for detecting, purifying, immobilizing, or removing, a protein containing a CH1-CL domain of immunoglobulin G, wherein said CH1-CL domain is in a non-native conformation, and wherein said kit comprises the polypeptide according to claim 1.

4. A polypeptide comprising the amino acid sequence of the following Formula 2:

(SEQ ID NO: 4)
Y-D-P-E-T-G-T-W-P-Q-x-I-x-L-x-[IL]-[NT]-[YW], wherein x represents an amino acid residue, and brackets represent any one of the amino acid residues within the brackets, and wherein the polypeptide has affinity for a CH1-CL domain of immunoglobulin G.

5. The polypeptide according to claim 4, wherein said polypeptide comprises the amino acid sequence of any one of SEQ ID NOs: 5, 6, and 36 to 41.

6. The polypeptide according to claim 4, wherein said polypeptide has 1-20 amino acid residues added to the N-terminus, the C-terminus, or both, of the amino acid sequence of Formula 2.

7. A polypeptide comprising the amino acid sequence of the following Formula 3:

P-N-S-G-G-G-S-Y-D-P-E-T-G-T-W-P-Q-x-I-x-L-x-[IL]-[NT]-[YW], (SEQ ID NO: 7)

wherein x represents an amino acid residue, and brackets represent any one of the amino acid residues within the brackets, and wherein the polypeptide has affinity for a CH1-CL domain of immunoglobulin G.

8. The polypeptide according to claim 7, wherein said polypeptide comprises the amino acid sequence of SEQ ID NO: 8 or 9.

9. The polypeptide according to claim 7, wherein said polypeptide has 1-20 amino acid residues added to the N-terminus, the C-terminus, or both, of the amino acid sequence of Formula 3.

10. A tandem polypeptide comprising a first polypeptide, and further comprising a second polypeptide at the amino-terminus, the carboxyl-terminus, or both termini thereof,
wherein said first polypeptide comprises the amino acid sequence of the following Formula 1:

P-Q-x-I-x-L-x-[IL]-[NT]-[YW] (SEQ ID NO: 1), wherein x represents an amino acid residue, and brackets represent any one of the amino acid residues within the brackets,
wherein said first polypeptide has affinity for a CH1-CL domain of immunoglobulin G, and
wherein the tandem polypeptide has affinity for a CH1-CL domain of immunoglobulin G.

11. A fusion protein having a protein bound to the amino-terminus, the carboxy-terminus, or both termini, of a polypeptide comprising the amino acid sequence of the following Formula 1:

P-Q-x-I-x-L-x-[IL]-[NT]-[YW] (SEQ ID NO: 1), wherein x represents an amino acid residue, and brackets represent any one of the amino acid residues within the brackets,
wherein said polypeptide has affinity for a CH1-CL domain of immunoglobulin G, and
wherein the fusion protein has affinity for a CH1-CL domain of immunoglobulin G.

12. The fusion protein according to claim 11, wherein said fusion protein comprises the amino acid sequence of any one of SEQ ID NOs: 14, 15, and 42 to 46.

13. A nucleic acid encoding the polypeptide according to claim 1.

14. A nucleic acid encoding the fusion protein according to claim 12, wherein the nucleic acid comprises the nucleotide sequence of any one of SEQ ID NOs: 17, 18, and 47 to 51.

15. A recombinant vector comprising the nucleic acid according to claim 13.

16. A transformant comprising the recombinant vector according to claim 15.

17. A recombinant phage or a recombinant virus comprising the nucleic acid according to claim 13.

18. A modified polypeptide, wherein said modified polypeptide comprises a polypeptide bound to an organic compound, an inorganic compound, or both,
wherein said polypeptide comprises the amino acid sequence of the following Formula 1:

P-Q-x-I-x-L-x-[IL]-[NT]-[YW] (SEQ ID NO: 1), wherein x represents an amino acid residue, and brackets represent any one of the amino acid residues within the brackets,
wherein said polypeptide has affinity for a CH1-CL domain of immunoglobulin G, and
wherein said modified polypeptide has affinity for a CH1-CL domain of immunoglobulin G.

19. An immobilized polypeptide, wherein said immobilized polypeptide comprises a polypeptide immobilized on a water-insoluble solid-phase support,
wherein said polypeptide comprises the amino acid sequence of the following Formula 1:

P-Q-x-I-x-L-x-[IL]-[NT]-[YW] (SEQ ID NO: 1), wherein x represents an amino acid residue, and brackets represent any one of the amino acid residues within the brackets, and
wherein said polypeptide has affinity for a CH1-CL domain of immunoglobulin G.

20. A method for detecting a protein containing a CH1-CL domain of immunoglobulin G, wherein said CH1-CL domain is in a non-native conformation, the method comprising:
(1) contacting a test sample suspected to be contaminated with said protein containing the CH1-CL domain, with a polypeptide comprising the amino acid sequence of the following Formula 1:

P-Q-x-I-x-L-x-[IL]-[NT]-[YW] (SEQ ID NO: 1), wherein x represents an amino acid residue, and brackets represent any one of the amino acid residues within the brackets, and
wherein said polypeptide has affinity for a CH1-CL domain of immunoglobulin G; and
(2) determining whether or not a bond is formed between said protein containing the CH1-CL domain and said polypeptide.

21. A method for purifying a protein containing a CH1-CL domain of immunoglobulin G, wherein said CH1-CL domain is in a non-native conformation, the method comprising:
(1) contacting a sample comprising said protein containing the CH1-CL domain with a polypeptide, to bind said protein containing the CH1-CL domain to said polypeptide, wherein said polypeptide comprises the amino acid sequence of the following Formula 1:

P-Q-x-I-x-L-x-[IL]-[NT]-[YW] (SEQ ID NO: 1), wherein x represents an amino acid residue, and brackets represent any one of the amino acid residues within the brackets, and
wherein said polypeptide has affinity for a CH1-CL domain of immunoglobulin G; and
(2) collecting the protein containing the CH1-CL domain bound to said polypeptide from the sample.

22. A method for removing a protein containing a CH1-CL domain of immunoglobulin G, wherein said CH1-CL domain is in a non-native conformation, the method comprising:
(1) contacting a sample comprising the protein containing the CH1-CL domain with a polypeptide, to bind the protein containing the CH1-CL domain to said polypeptide, wherein said polypeptide comprises the amino acid sequence of the following Formula 1:

P-Q-x-I-x-L-x-[IL]-[NT]-[YW] (SEQ ID NO: 1), wherein x represents an amino acid residue, and brackets represent any one of the amino acid residues within the brackets, and wherein said polypeptide has affinity for a CH1-CL domain of immunoglobulin G; and (2) removing the protein containing the CH1-CL domain bound to said polypeptide.

\* \* \* \* \*

SEQUENCE LISTING

```
<160> NUMBER OF SEQ ID NOS: 51

<210> SEQ ID NO 1
<211> LENGTH: 10
<212> TYPE: PRT
<213> ORGANISM: Artificial Sequence
<220> FEATURE:
<223> OTHER INFORMATION: Synthetic IgG binding peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
```

```
<222> LOCATION: (8)..(8)
<223> OTHER INFORMATION: Xaa is Ile or Leu
<220> FEATURE:
<221> NAME/KEY: misc_feature
<222> LOCATION: (9)..(9)
<223> OTHER INFORMATION: Xaa is Asn or Thr
<220> FEATURE:
<221> NAME/KEY: misc_feature
<222> LOCATION: (10)..(10)
<223> OTHER INFORMATION: Xaa is Tyr or Trp

<400> SEQUENCE: 1

Pro Gln Xaa Ile Xaa Leu Xaa Xaa Xaa Xaa
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic IgG binding peptide

<400> SEQUENCE: 2

Pro Gln Glu Ile Arg Leu Ile Leu Asn Trp
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic IgG binding peptide

<400> SEQUENCE: 3

Pro Gln Trp Ile Thr Leu Thr Ile Thr Tyr
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Synthetic IgG binding peptide
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa is Ile or Leu
<220> FEATURE:
<221> NAME/KEY: misc_feature
<222> LOCATION: (17)..(17)
<223> OTHER INFORMATION: Xaa is Asn or Thr
<220> FEATURE:
<221> NAME/KEY: misc_feature
<222> LOCATION: (18)..(18)
<223> OTHER INFORMATION: Xaa is Tyr or Trp

<400> SEQUENCE: 4

Tyr Asp Pro Glu Thr Gly Thr Trp Pro Gln Xaa Ile Xaa Leu Xaa Xaa
1               5                   10                  15
```

Xaa Xaa

<210> SEQ ID NO 5
<211> LENGTH: 18
<212> TYPE: PRT
<213> ORGANISM: Artificial Sequence
<220> FEATURE:
<223> OTHER INFORMATION: Synthetic IgG binding peptide

<400> SEQUENCE: 5

Tyr Asp Pro Glu Thr Gly Thr Trp Pro Gln Glu Ile Arg Leu Ile Leu
1               5                   10                  15

Asn Trp

<210> SEQ ID NO 6
<211> LENGTH: 18
<212> TYPE: PRT
<213> ORGANISM: Artificial Sequence
<220> FEATURE:
<223> OTHER INFORMATION: Synthetic IgG binding peptide

<400> SEQUENCE: 6

Tyr Asp Pro Glu Thr Gly Thr Trp Pro Gln Trp Ile Thr Leu Thr Ile
1               5                   10                  15

Thr Tyr

<210> SEQ ID NO 7
<211> LENGTH: 26
<212> TYPE: PRT
<213> ORGANISM: Artificial Sequence
<220> FEATURE:
<223> OTHER INFORMATION: Synthetic IgG binding peptide
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa is Ile or Leu
<220> FEATURE:
<221> NAME/KEY: misc_feature
<222> LOCATION: (25)..(25)
<223> OTHER INFORMATION: Xaa is Asn or Thr
<220> FEATURE:
<221> NAME/KEY: misc_feature
<222> LOCATION: (26)..(26)
<223> OTHER INFORMATION: Xaa is Tyr or Trp

<400> SEQUENCE: 7

Pro Asn Ser Gly Gly Gly Gly Ser Tyr Asp Pro Glu Thr Gly Thr Trp
1               5                   10                  15

Pro Gln Xaa Ile Xaa Leu Xaa Xaa Xaa Xaa
            20                  25

<210> SEQ ID NO 8
<211> LENGTH: 26
<212> TYPE: PRT
<213> ORGANISM: Artificial Sequence
<220> FEATURE:
<223> OTHER INFORMATION: Synthetic IgG binding peptide

```
<400> SEQUENCE: 8

Pro Asn Ser Gly Gly Gly Gly Ser Tyr Asp Pro Glu Thr Gly Thr Trp
1               5                   10                  15

Pro Gln Glu Ile Arg Leu Ile Leu Asn Trp
            20                  25

<210> SEQ ID NO 9
<211> LENGTH: 26
<212> TYPE: PRT
<213> ORGANISM: Artificial Sequence
<220> FEATURE:
<223> OTHER INFORMATION: Synthetic IgG binding peptide

<400> SEQUENCE: 9

Pro Asn Ser Gly Gly Gly Gly Ser Tyr Asp Pro Glu Thr Gly Thr Trp
1               5                   10                  15

Pro Gln Trp Ile Thr Leu Thr Ile Thr Tyr
            20                  25

<210> SEQ ID NO 10
<211> LENGTH: 26
<212> TYPE: PRT
<213> ORGANISM: Artificial Sequence
<220> FEATURE:
<223> OTHER INFORMATION: Synthetic IgG binding peptide

<400> SEQUENCE: 10

Pro Asn Ser Gly Gly Gly Gly Ser Tyr Asp Pro Glu Thr Gly Thr Trp
1               5                   10                  15

Ala Gln Glu Ile Arg Leu Ile Leu Asn Trp
            20                  25

<210> SEQ ID NO 11
<211> LENGTH: 26
<212> TYPE: PRT
<213> ORGANISM: Artificial Sequence
<220> FEATURE:
<223> OTHER INFORMATION: Synthetic IgG binding peptide

<400> SEQUENCE: 11

Pro Asn Ser Gly Gly Gly Gly Ser Tyr Asp Pro Glu Thr Gly Thr Trp
1               5                   10                  15

Pro Ala Glu Ile Arg Leu Ile Leu Asn Trp
            20                  25

<210> SEQ ID NO 12
<211> LENGTH: 26
<212> TYPE: PRT
<213> ORGANISM: Artificial Sequence
<220> FEATURE:
<223> OTHER INFORMATION: Synthetic IgG binding peptide

<400> SEQUENCE: 12

Pro Asn Ser Gly Gly Gly Gly Ser Tyr Asp Pro Glu Thr Gly Thr Trp
1               5                   10                  15

Pro Gln Glu Ile Arg Leu Ile Ala Asn Trp
            20                  25

<210> SEQ ID NO 13
<211> LENGTH: 183
<212> TYPE: PRT
<213> ORGANISM: Artificial Sequence
<220> FEATURE:
```

<223> OTHER INFORMATION: Synthetic IgG binding peptide

<400> SEQUENCE: 13

Met Ser Asp Lys Ile Ile His Leu Thr As

Gly Gly Gly Gly Ser Tyr Asp Pro Glu Thr Gly Thr Trp Pro Gln Glu
            165                 170                 175

Ile Arg Leu Ile Leu Asn Trp
            180

<210> SEQ ID NO 15
<211> LENGTH: 183
<212> TYPE: PRT
<213> ORGANISM: Artificial Sequence
<220> FEATURE:
<223> OTHER INFORMATION: Synthetic IgG binding peptide

<400> SEQUENCE: 15

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Tyr Asp Pro Glu Thr Gly Thr Trp Pro Gln Trp
            165                 170                 175

Ile Thr Leu Thr Ile Thr Tyr
            180

<210> SEQ ID NO 16
<211> LENGTH: 549
<212> TYPE: DNA
<213> ORGANISM: Artificial Sequence
<220> FEATURE:
<223> OTHER INFORMATION: Synthetic oligonucleotide sequence

<400> SEQUENCE: 16
atgagcgata aaattattca cctgactgac gacagttttg acacggatgt actcaaagcg      60
gacggggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggccggt tctggttctg gccatactag tggtggtggc     360
ggttctaata acaatcctcc tactcctact ccatcgagtg gttctggtca tcaccatcac     420
catcactccg cggctcttga agtcctcttt cagggacccg gtaccaggat ccgaattcg      480

```
ggaggagggg gatcatacga ccccgagacg ggcacgtggc cacaagcaca gaaaaaagag    540
atacaaaca                                                            549
```

<210> SEQ ID NO 17
<211> LENGTH: 549
<212> TYPE: DNA
<213> ORGANISM: Artificial Sequence
<220> FEATURE:
<223> OTHER INFORMATION: Synthetic oligonucleotide sequence

<400> SEQUENCE: 17

```
atgagcgata aaattattca cctgactgac gacagttttg acacggatgt actcaaagcg     60 gacgggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg gtaccagga tccgaattcg    480 ggaggagggg gatcatacga ccccgagacg ggcacgtggc cacaggaaat tagactaata    540
cttaattgg                                                           549
```

<210> SEQ ID NO 18
<211> LENGTH: 549
<212> TYPE: DNA
<213> ORGANISM: Artificial Sequence
<220> FEATURE:
<223> OTHER INFORMATION: Synthetic oligonucleotide sequence

<400> SEQUENCE: 18

```
atgagcgata aaattattca cctgactgac gacagttttg acacggatgt actcaaagcg     60 gacgggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg gtaccagga tccgaattcg    480 ggaggagggg gatcatacga ccccgagacg ggcacgtggc cgcagtggat aactcttacg    540
ataacgtat                                                           549
```

<210> SEQ ID NO 19
<211> LENGTH: 109
<212> TYPE: PRT
<213> ORGANISM: Homo sapiens

<400> SEQUENCE: 19

```
Met His His His His His His Ser Thr Lys Gly Pro Ser Val Phe Pro
  1               5                  10                  15

Leu Ala Pro Ser Ser Lys Ser Thr Ser Gly Gly Thr Ala Ala Leu Gly
             20                  25                  30

Cys Leu Val Lys Asp Tyr Phe Pro Glu Pro Val Thr Val Ser Trp Asn
```

```
                35                  40                  45
Ser Gly Ala Leu Thr Ser Gly Val His Thr Phe Pro Ala Val Leu Gln
             50                  55                  60
Ser Ser Gly Leu Tyr Ser Leu Ser Ser Val Val Thr Val Pro Ser Ser
 65                  70                  75                  80
Ser Leu Gly Thr Gln Thr Tyr Ile Cys Asn Val Asn His Lys Pro Ser
                 85                  90                  95
Asn Thr Lys Val Asp Lys Lys Val Glu Pro Lys Ser Cys
            100                 105
```

<210> SEQ ID NO 20
<211> LENGTH: 114
<212> TYPE: PRT
<213> ORGANISM: Homo sapiens

<400> SEQUENCE: 20

```
Met His His His His His Lys Arg Thr Val Ala Pro Ser Val Phe
 1               5                  10                  15
Ile Phe Pro Pro Ser Asp Glu Gln Leu Lys Ser Gly Thr Ala Ser Val
                 20                  25                  30
Val Cys Leu Leu Asn Asn Phe Tyr Pro Arg Glu Ala Lys Val Gln Trp
             35                  40                  45
Lys Val Asp Asn Ala Leu Gln Ser Gly Asn Ser Gln Glu Ser Val Thr
 50                  55                  60
Glu Gln Asp Ser Lys Asp Ser Thr Tyr Ser Leu Ser Ser Thr Leu Thr
 65                  70                  75                  80
Leu Ser Lys Ala Asp Tyr Glu Lys His Lys Val Tyr Ala Cys Glu Val
                 85                  90                  95
Thr His Gln Gly Leu Ser Ser Pro Val Thr Lys Ser Phe Asn Arg Gly
            100                 105                 110
Glu Cys
```

<210> SEQ ID NO 21
<211> LENGTH: 23
<212> TYPE: PRT
<213> ORGANISM: Artificial Sequence
<220> FEATURE:
<223> OTHER INFORMATION: Synthetic peptide library
<220> FEATURE:
<221> NAME/KEY: misc_feature
<222> LOCATION: (14)..(23)
<223> OTHER INFORMATION: Xaa can be any naturally occurring amino acid

<400> SEQUENCE: 21

```
Gly Gly Gly Gly Ser Tyr Asp Pro Glu Thr Gly Thr Trp Xaa Xaa Xaa
 1               5                  10                  15
Xaa Xaa Xaa Xaa Xaa Xaa Xaa
            20
```

<210> SEQ ID NO 22
<211> LENGTH: 21
<212> TYPE: PRT
<213> ORGANISM: Artificial Sequence
<220> FEATURE:
<223> OTHER INFORMATION: Synthetic peptide library
<220> FEATURE:
<221> NAME/KEY: misc_feature
<222> LOCATION: (14)..(21)
<223> OTHER INFORMATION: Xaa can be any naturally occurring amino acid

<400> SEQUENCE: 22

```
Gly Gly Gly Gly Ser Tyr Asp Pro Glu Thr Gly Thr Trp Xaa Xaa Xaa
1               5                   10                  15

Xaa Xaa Xaa Xaa Xaa
            20
```

<210> SEQ ID NO 23
<211> LENGTH: 24
<212> TYPE: PRT
<213> ORGANISM: Artificial Sequence
<220> FEATURE:
<223> OTHER INFORMATION: Synthetic peptide library
<220> FEATURE:
<221> NAME/KEY: misc_feature
<222> LOCATION: (16)..(24)
<223> OTHER INFORMATION: Xaa can be any naturally occurring amino acid

<400> SEQUENCE: 23

```
Gly Gly Gly Gly Ser Tyr Tyr Asp Pro Glu Thr Gly Thr Trp Tyr Xaa
1               5                   10                  15

Xaa Xaa Xaa Xaa Xaa Xaa Xaa Xaa
            20
```

<210> SEQ ID NO 24
<211> LENGTH: 23
<212> TYPE: PRT
<213> ORGANISM: Artificial Sequence
<220> FEATURE:
<223> OTHER INFORMATION: Synthetic peptide library
<220> FEATURE:
<221> NAME/KEY: misc_feature
<222> LOCATION: (16)..(23)
<223> OTHER INFORMATION: Xaa can be any naturally occurring amino acid

<400> SEQUENCE: 24

```
Gly Gly Gly Gly Ser Tyr Tyr Asp Pro Glu Thr Gly Thr Trp Tyr Xaa
1               5                   10                  15

Xaa Xaa Xaa Xaa Xaa Xaa Xaa
            20
```

<210> SEQ ID NO 25
<211> LENGTH: 69
<212> TYPE: DNA
<213> ORGANISM: Artificial Sequence
<220> FEATURE:
<223> OTHER INFORMATION: Synthetic oligonucleotide sequence
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (42)..(42)
<223> OTHER INFORMATION: k is g or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (45)..(45)
<223> OTHER INFORMATION: k is g or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: k is g or t
<220> FEATURE:
<221> NAME/KEY: misc_feature

```
<222> LOCATION: (49)..(50)
<223> OTHER INFORMATION: n is a, c, g, or t
<220> FEATURE:
<221> NAME/KEY: misc_feature
<222> LOCATION: (51)..(51)
<223> OTHER INFORMATION: k is g or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (54)..(54)
<223> OTHER INFORMATION: k is g or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (57)..(57)
<223> OTHER INFORMATION: k is g or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (60)..(60)
<223> OTHER INFORMATION: k is g or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (63)..(63)
<223> OTHER INFORMATION: k is g or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (66)..(66)
<223> OTHER INFORMATION: k is g or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (69)..(69)
<223> OTHER INFORMATION: k is g or t

<400> SEQUENCE: 25
ggaggagggg gatcatacga ccccgagacg ggcacgtggn nknnknnknn knnknnknnk    60 nnknnknnk                                                            69

<210> SEQ ID NO 26
<211> LENGTH: 63
<212> TYPE: DNA
<213> ORGANISM: Artificial Sequence
<220> FEATURE:
<223> OTHER INFORMATION: Synthetic oligonucleotide sequence
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (42)..(42)
<223> OTHER INFORMATION: k is g or t
<220> FEATURE:
<221> NAME/KEY: misc_feature
<222> LOCATION: (43)..(44)
```

<223> OTHER INFORMATION: n is a, c, g, or t
<220> FEATURE:
<221> NAME/KEY: misc_feature
<222> LOCATION: (45)..(45)
<223> OTHER INFORMATION: k is g or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: k is g or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (51)..(51)
<223> OTHER INFORMATION: k is g or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (54)..(54)
<223> OTHER INFORMATION: k is g or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (57)..(57)
<223> OTHER INFORMATION: k is g or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (60)..(60)
<223> OTHER INFORMATION: k is g or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (63)..(63)
<223> OTHER INFORMATION: k is g or t

<400> SEQUENCE: 26
ggaggagggg gatcatacga ccccgagacg ggcacgtggn nknnknnknn knnknnknnk    60 nnk    63

<210> SEQ ID NO 27
<211> LENGTH: 75
<212> TYPE: DNA
<213> ORGANISM: Artificial Sequence
<220> FEATURE:
<223> OTHER INFORMATION: Synthetic oligonucleotide sequence
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: k is g or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (51)..(51)
<223> OTHER INFORMATION: k is g or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (54)..(54)
<223> OTHER INFORMATION: k is g or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (57)..(57)
<223> OTHER INFORMATION: k is g or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (60)..(60)
<223> OTHER INFORMATION: k is g or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (63)..(63)
<223> OTHER INFORMATION: k is g or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (66)..(66)
<223> OTHER INFORMATION: k is g or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (69)..(69)
<223> OTHER INFORMATION: k is g or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (72)..(72)
<223> OTHER INFORMATION: k is g or t
<220> FEATURE:
<221> NAME/KEY: misc_feature
<222> LOCATION: (73)..(74)
<223> OTHER INFORMATION: n is a, c, g, or t
<220> FEATURE:
<221> NAME/KEY: misc_feature
<222> LOCATION: (75)..(75)
<223> OTHER INFORMATION: k is g or t

<400> SEQUENCE: 27
ggaggagggg gatcatacta tgaccccgag acgggcacgt ggtatnnknn knnknnknnk      60
nnknnknnkn nknnk                                                      75

<210> SEQ ID NO 28
<211> LENGTH: 69
<212> TYPE: DNA

```
<213> ORGANISM: Artificial Sequence
<220> FEATURE:
<223> OTHER INFORMATION: Synthetic oligonucleotide sequence
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: k is g or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (51)..(51)
<223> OTHER INFORMATION: k is g or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (54)..(54)
<223> OTHER INFORMATION: k is g or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (57)..(57)
<223> OTHER INFORMATION: k is g or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (60)..(60)
<223> OTHER INFORMATION: k is g or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (63)..(63)
<223> OTHER INFORMATION: k is g or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (66)..(66)
<223> OTHER INFORMATION: k is g or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (69)..(69)
<223> OTHER INFORMATION: k is g or t

<400> SEQUENCE: 28
ggaggagggg gatcatacta tgaccccgag acgggcacgt ggtatnnknn knnknnknnk      60 nnknnknnk                                                              69

<210> SEQ ID NO 29
<211> LENGTH: 157
<212> TYPE: PRT
<213> ORGANISM: Escherichia coli
```

<400> SEQUENCE: 29

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
                35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
                100                 105                 110

Ser Gly His Thr Ser Gly Gly Gly Ser Asn Asn Asn Pro Pro Thr
                115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp
145                 150                 155

<210> SEQ ID NO 30
<211> LENGTH: 8
<212> TYPE: PRT
<213> ORGANISM: Artificial Sequence
<220> FEATURE:
<223> OTHER INFORMATION: synthetic peptide

<400> SEQUENCE: 30

Pro Asn Ser Gly Gly Gly Gly Ser
1               5

<210> SEQ ID NO 31
<211> LENGTH: 8
<212> TYPE: PRT
<213> ORGANISM: Artificial Sequence
<220> FEATURE:
<223> OTHER INFORMATION: synthetic peptide

<400> SEQUENCE: 31

Tyr Asp Pro Glu Thr Gly Thr Trp
1               5

<210> SEQ ID NO 32
<211> LENGTH: 10
<212> TYPE: PRT
<213> ORGANISM: Artificial Sequence
<220> FEATURE:
<223> OTHER INFORMATION: Synthetic IgG binding peptide

<400> SEQUENCE: 32

Pro Gln Ala Gln Lys Lys Glu Ile Gln Thr
1               5                   10

<210> SEQ ID NO 33
<211> LENGTH: 16
<212> TYPE: PRT
<213> ORGANISM: Artificial Sequence
<220> FEATURE:
<223> OTHER INFORMATION: synthetic peptide

```
<400> SEQUENCE: 33

Pro Asn Ser Gly Gly Gly Gly Ser Tyr Asp Pro Glu Thr Gly Thr Trp
1               5                   10                  15

<210> SEQ ID NO 34
<211> LENGTH: 28
<212> TYPE: PRT
<213> ORGANISM: Artificial Sequence
<220> FEATURE:
<223> OTHER INFORMATION: Synthetic peptide library
<220> FEATURE:
<221> NAME/KEY: misc_feature
<222> LOCATION: (1)..(10)
<223> OTHER INFORMATION: Xaa can be any naturally occurring amino acid

<400> SEQUENCE: 34

Xaa Xaa Xaa Xaa Xaa Xaa Xaa Xaa Xaa Xaa Tyr Asp Pro Glu Thr Gly
1               5                   10                  15

Thr Trp Pro Gln Glu Ile Arg Leu Ile Leu Asn Trp
            20                  25

<210> SEQ ID NO 35
<211> LENGTH: 84
<212> TYPE: DNA
<213> ORGANISM: Artificial Sequence
<220> FEATURE:
<223> OTHER INFORMATION: Synthetic olignucleotide sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (3)..(3)
<223> OTHER INFORMATION: k is g or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (6)..(6)
<223> OTHER INFORMATION: k is g or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (9)..(9)
<223> OTHER INFORMATION: k is g or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (12)..(12)
<223> OTHER INFORMATION: k is g or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (15)..(15)
<223> OTHER INFORMATION: k is g or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
```

```
<222> LOCATION: (18)..(18)
<223> OTHER INFORMATION: k is g or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: k is g or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (27)..(27)
<223> OTHER INFORMATION: k is g or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (30)..(30)
<223> OTHER INFORMATION: k is g or t

<400> SEQUENCE: 35
nnknnknnkn nknnknnknn knnknnknnk tacgacaccg agacgggcac gtggccgcag    60
gaaattcgcc tgattctgaa ctgg                                          84

<210> SEQ ID NO 36
<211> LENGTH: 28
<212> TYPE: PRT
<213> ORGANISM: Artificial Sequence
<220> FEATURE:
<223> OTHER INFORMATION: Synthetic IgG binding peptide

<400> SEQUENCE: 36

His Asn Phe Thr Leu Pro Leu Trp Met Tyr Tyr Asp Pro Glu Thr Gly
1               5                   10                  15

Thr Trp Pro Gln Glu Ile Arg Leu Ile Leu Asn Trp
            20                  25

<210> SEQ ID NO 37
<211> LENGTH: 28
<212> TYPE: PRT
<213> ORGANISM: Artificial Sequence
<220> FEATURE:
<223> OTHER INFORMATION: Synthetic IgG binding peptide

<400> SEQUENCE: 37

Arg Phe Pro Leu Met Phe Gly Pro Ser Trp Tyr Asp Pro Glu Thr Gly
1               5                   10                  15

Thr Trp Pro Gln Glu Ile Arg Leu Ile Leu Asn Trp
            20                  25

<210> SEQ ID NO 38
<211> LENGTH: 28
<212> TYPE: PRT
<213> ORGANISM: Artificial Sequence
<220> FEATURE:
```

```
<223> OTHER INFORMATION: Synthetic IgG binding peptide

<400> SEQUENCE: 38

Arg Phe Tyr Val Leu Leu Asp Ser Ser Trp Tyr Asp Pro Glu Thr Gly
1               5                   10                  15

Thr Trp Pro Gln Glu Ile Arg Leu Ile Leu Asn Trp
            20                  25

<210> SEQ ID NO 39
<211> LENGTH: 28
<212> TYPE: PRT
<213> ORGANISM: Artificial Sequence
<220> FEATURE:
<223> OTHER INFORMATION: Synthetic IgG binding peptide

<400> SEQUENCE: 39

Val Ser Lys Phe Tyr Pro Leu Trp Thr Arg Tyr Asp Pro Glu Thr Gly
1               5                   10                  15

Thr Trp Pro Gln Glu Ile Arg Leu Ile Leu Asn Trp
            20                  25

<210> SEQ ID NO 40
<211> LENGTH: 28
<212> TYPE: PRT
<213> ORGANISM: Artificial Sequence
<220> FEATURE:
<223> OTHER INFORMATION: Synthetic IgG binding peptide

<400> SEQUENCE: 40

Val Phe Leu Val Leu Met Gly Pro Glu Phe Tyr Asp Pro Glu Thr Gly
1               5                   10                  15

Thr Trp Pro Gln Glu Ile Arg Leu Ile Leu Asn Trp
            20                  25

<210> SEQ ID NO 41
<211> LENGTH: 28
<212> TYPE: PRT
<213> ORGANISM: Artificial Sequence
<220> FEATURE:
<223> OTHER INFORMATION: Synthetic IgG binding peptide

<400> SEQUENCE: 41

Phe Leu Leu Phe Cys Pro Arg Ser Leu Cys Tyr Asp Pro Glu Thr Gly
1               5                   10                  15

Thr Trp Pro Gln Glu Ile Arg Leu Ile Leu Asn Trp
            20                  25

<210> SEQ ID NO 42
<211> LENGTH: 193
<212> TYPE: PRT
<213> ORGANISM: Artificial Sequence
<220> FEATURE:
<223> OTHER INFORMATION: Synthetic IgG binding peptide

<400> SEQUENCE: 42

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60
```

```
Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His Ser Ala
            130                 135                 140

Ala Leu Glu Val Leu Phe Gln Gly Pro Gly Tyr Gln Asp Pro Asn Ser
145                 150                 155                 160

Gly Gly Gly Gly Ser His Asn Phe Thr Leu Pro Leu Trp Met Tyr Tyr
                165                 170                 175

Asp Pro Glu Thr Gly Thr Trp Pro Gln Glu Ile Arg Leu Ile Leu Asn
            180                 185                 190

Trp
```

```
<210> SEQ ID NO 43
<211> LENGTH: 193
<212> TYPE: PRT
<213> ORGANISM: Artificial Sequence
<220> FEATURE:
<223> OTHER INFORMATION: Synthetic IgG binding peptide

<400> SEQUENCE: 43
```

```
Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
 50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His Ser Ala
            130                 135                 140

Ala Leu Glu Val Leu Phe Gln Gly Pro Gly Tyr Gln Asp Pro Asn Ser
145                 150                 155                 160

Gly Gly Gly Gly Ser Arg Phe Pro Leu Met Phe Gly Pro Ser Trp Tyr
                165                 170                 175

Asp Pro Glu Thr Gly Thr Trp Pro Gln Glu Ile Arg Leu Ile Leu Asn
            180                 185                 190

Trp
```

```
<210> SEQ ID NO 44
<211> LENGTH: 193
<212> TYPE: PRT
```

<213> ORGANISM: Artificial Sequence
<220> FEATURE:
<223> OTHER INFORMATION: Synthetic IgG binding peptide

<400> SEQUENCE: 44

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Arg Phe Tyr Val Leu Leu Asp Ser Ser Trp Tyr
                165                 170                 175

Asp Pro Glu Thr Gly Thr Trp Pro Gln Glu Ile Arg Leu Ile Leu Asn
            180                 185                 190

Trp
```

<210> SEQ ID NO 45
<211> LENGTH: 193
<212> TYPE: PRT
<213> ORGANISM: Artificial Sequence
<220> FEATURE:
<223> OTHER INFORMATION: Synthetic IgG binding peptide

<400> SEQUENCE: 45

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His Ser Ala
```

```
Ala Leu Glu Val Leu Phe Gln Gly Pro Gly Tyr Gln Asp Pro Asn Ser
145                 150                 155                 160

Gly Gly Gly Gly Ser Val Ser Lys Phe Tyr Pro Leu Trp Thr Arg Tyr
                165                 170                 175

Asp Pro Glu Thr Gly Thr Trp Pro Gln Glu Ile Arg Leu Ile Leu Asn
            180                 185                 190

Trp

<210> SEQ ID NO 46
<211> LENGTH: 193
<212> TYPE: PRT
<213> ORGANISM: Artificial Sequence
<220> FEATURE:
<223> OTHER INFORMATION: Synthetic IgG binding peptide

<400> SEQUENCE: 46

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Val Phe Leu Val Leu Met Gly Pro Glu Phe Tyr
                165                 170                 175

Asp Pro Glu Thr Gly Thr Trp Pro Gln Glu Ile Arg Leu Ile Leu Asn
            180                 185                 190

Trp

<210> SEQ ID NO 47
<211> LENGTH: 579
<212> TYPE: DNA
<213> ORGANISM: Artificial Sequence
<220> FEATURE:
<223> OTHER INFORMATION: Synthetic oligonucleotide sequence

<400> SEQUENCE: 47
atgagcgata aaattattca cctgactgac gacagttttg acacggatgt actcaaagcg        60 gacgggcga tcctcgtcga tttctgggca gagtggtgcg gtccgtgcaa aatgatcgcc       120
ccgattctgg atgaaatcgc tgacgaatat cagggcaaac tgaccgttgc aaaactgaac       180
atcgatcaaa accctggcac tgcgccgaaa tatggcatcc gtggtatccc gactctgctg       240
```

```
ctgttcaaaa acggtgaagt ggcggcaacc aaagtgggtg cactgtctaa aggtcagttg      300
aaagagttcc tcgacgctaa cctggccggt tctggttctg gccatactag tggtggtggc      360
ggttctaata acaatcctcc tactcctact ccatctagtg gttctggtca tcaccatcac      420
catcactccg cggctcttga agtcctcttt cagggacccg ggtaccagga tccgaattcg      480
ggaggagggg gatcacataa ttttactctt cctctgtgga tgtattacga ccccgagacg      540
ggcacgtggc cgcaggaaat tcgcctgatt ctgaactgg                             579
```

<210> SEQ ID NO 48
<211> LENGTH: 579
<212> TYPE: DNA
<213> ORGANISM: Artificial Sequence
<220> FEATURE:
<223> OTHER INFORMATION: Synthetic oligonucleotide sequence

<400> SEQUENCE: 48

```
atgagcgata aaattattca cctgactgac gacagttttg acacggatgt actcaaagcg       60 gacgggcga tcctcgtcga tttctgggca gagtggtgcg gtccgtgcaa aatgatcgcc       120
ccgattctgg atgaaatcgc tgacgaatat cagggcaaac tgaccgttgc aaaactgaac      180
atcgatcaaa accctggcac tgcgccgaaa tatggcatcc gtggtatccc gactctgctg      240
ctgttcaaaa acggtgaagt ggcggcaacc aaagtgggtg cactgtctaa aggtcagttg      300
aaagagttcc tcgacgctaa cctggccggt tctggttctg gccatactag tggtggtggc      360
ggttctaata acaatcctcc tactcctact ccatctagtg gttctggtca tcaccatcac      420
catcactccg cggctcttga agtcctcttt cagggacccg ggtaccagga tccgaattcg      480
ggaggagggg gatcacgttt tccgttgatg tttgggccgt cttggtacga ccccgagacg      540
ggcacgtggc cgcaggaaat tcgcctgatt ctgaactgg                             579
```

<210> SEQ ID NO 49
<211> LENGTH: 579
<212> TYPE: DNA
<213> ORGANISM: Artificial Sequence
<220> FEATURE:
<223> OTHER INFORMATION: Synthetic oligonucleotide sequence

<400> SEQUENCE: 49

```
atgagcgata aaattattca cctgactgac gacagttttg acacggatgt actcaaagcg       60 gacgggcga tcctcgtcga tttctgggca gagtggtgcg gtccgtgcaa aatgatcgcc       120
ccgattctgg atgaaatcgc tgacgaatat cagggcaaac tgaccgttgc aaaactgaac      180
atcgatcaaa accctggcac tgcgccgaaa tatggcatcc gtggtatccc gactctgctg      240
ctgttcaaaa acggtgaagt ggcggcaacc aaagtgggtg cactgtctaa aggtcagttg      300
aaagagttcc tcgacgctaa cctggccggt tctggttctg gccatactag tggtggtggc      360
ggttctaata acaatcctcc tactcctact ccatctagtg gttctggtca tcaccatcac      420
catcactccg cggctcttga agtcctcttt cagggacccg ggtaccagga tccgaattcg      480
ggaggagggg gatcacggtt ttatgttctg ctggattctt cttggtacga ccccgagacg      540
ggcacgtggc cgcaggaaat tcgcctgatt ctgaactgg                             579
```

<210> SEQ ID NO 50
<211> LENGTH: 579
<212> TYPE: DNA
<213> ORGANISM: Artificial Sequence
<220> FEATURE:
<223> OTHER INFORMATION: Synthetic oligonucleotide sequence

```
<400> SEQUENCE: 50
atgagcgata aaattattca cctgactgac gacagttttg acacggatgt actcaaagcg        60
gacggggcga tcctcgtcga tttctgggca gagtggtgcg gtccgtgcaa aatgatcgcc       120
ccgattctgg atgaaatcgc tgacgaatat cagggcaaac tgaccgttgc aaaactgaac       180
atcgatcaaa accctggcac tgcgccgaaa tatggcatcc gtggtatccc gactctgctg       240
ctgttcaaaa acggtgaagt ggcggcaacc aaagtgggtg cactgtctaa aggtcagttg       300
aaagagttcc tcgacgctaa cctggccggt tctggttctg gccatactag tggtggtggc       360
ggttctaata acaatcctcc tactcctact ccatctagtg gttctggtca tcaccatcac       420
catcactccg cggctcttga agtcctcttt cagggacccg gtaccagga tccgaattcg       480 ggaggagggg gatcagtgag taagttttat ccgctgtgga cgcggtacga ccccgagacg       540
ggcacgtggc cgcaggaaat tcgcctgatt ctgaactgg                              579

<210> SEQ ID NO 51
<211> LENGTH: 579
<212> TYPE: DNA
<213> ORGANISM: Artificial Sequence
<220> FEATURE:
<223> OTHER INFORMATION: Synthetic oligonucleotide sequence

<400> SEQUENCE: 51
atgagcgata aaattattca cctgactgac gacagttttg acacggatgt actcaaagcg        60
gacggggcga tcctcgtcga tttctgggca gagtggtgcg gtccgtgcaa aatgatcgcc       120
ccgattctgg atgaaatcgc tgacgaatat cagggcaaac tgaccgttgc aaaactgaac       180
atcgatcaaa accctggcac tgcgccgaaa tatggcatcc gtggtatccc gactctgctg       240
ctgttcaaaa acggtgaagt ggcggcaacc aaagtgggtg cactgtctaa aggtcagttg       300
aaagagttcc tcgacgctaa cctggccggt tctggttctg gccatactag tggtggtggc       360
ggttctaata acaatcctcc tactcctact ccatctagtg gttctggtca tcaccatcac       420
catcactccg cggctcttga agtcctcttt cagggacccg gtaccagga tccgaattcg       480 ggaggagggg gatcagtgtt tcttgttttg atggggcctg agttttacga ccccgagacg       540
ggcacgtggc cgcaggaaat tcgcctgatt ctgaactgg                              579
```